United States Patent
Low et al.

(10) Patent No.: US 7,283,610 B2
(45) Date of Patent: Oct. 16, 2007

(54) ENHANCED MICRO-RADIATION THERAPY AND A METHOD OF MICRO-IRRADIATING BIOLOGICAL SYSTEMS

(75) Inventors: Daniel A. Low, St. Louis, MO (US); Perry W. Grigsby, St. Louis, MO (US)

(73) Assignee: Washington University in St. Louis, St. Louis, MO (US)

(*) Notice: Subject to any disclaimer, the term of this patent is extended or adjusted under 35 U.S.C. 154(b) by 64 days.

(21) Appl. No.: 10/843,086

(22) Filed: May 11, 2004

(65) Prior Publication Data

US 2005/0008121 A1    Jan. 13, 2005

Related U.S. Application Data

(60) Provisional application No. 60/470,335, filed on May 14, 2003.

(51) Int. Cl.
*A61N 5/10* (2006.01)
(52) U.S. Cl. .......................... 378/65; 378/197
(58) Field of Classification Search ................ 378/65, 378/68, 197, 196, 198; 250/492.1, 492.3; 600/2, 3, 411, 427
See application file for complete search history.

(56) References Cited

U.S. PATENT DOCUMENTS

| | | | | |
|---|---|---|---|---|
| 3,073,960 A | * | 1/1963 | Guentner et al. | ............. 378/65 |
| 5,339,347 A | * | 8/1994 | Slatkin et al. | ................. 378/65 |
| 5,373,844 A | * | 12/1994 | Smith et al. | ................... 378/65 |
| 5,635,721 A | * | 6/1997 | Bardi et al. | .................... 378/65 |
| 6,059,714 A | * | 5/2000 | Armini et al. | .................. 600/3 |
| 6,134,296 A | * | 10/2000 | Siochi | ........................... 378/65 |
| 6,512,813 B1 | * | 1/2003 | Krispel et al. | ................. 378/65 |
| 2003/0125283 A1 | * | 7/2003 | Gatenby | ...................... 514/44 |

OTHER PUBLICATIONS

Dilmanian et al., "Microbeam Radiation Therapy at the National Synchrotron Light Source", Recent Advances in Medical Applications of Synchrotron Radiation, Stanford Synchrotron Radiation Laboratory, Mar. 4-5, 2002 [retrieved from May 12, 2002]. Retrieved from the Internet:<URL: http://www-ssrl.slac.stanford.edu/special/dilmanian-abstract.html>.*
Iwata et al., "Design and Utility of a Small Animal CT/SPECT System", Nuclear Science Symposium Conference Record, 2001 IEEE, vol. 3, Nov. 4-10, 2001, pp. 1849-1852.*
National Research Council Canada, http://www.irs.inms.nrc.ca/inms/irs/BEAM/beamhome.html, Jan. 1, 2006.*
Table of Radioactive Isotopes, Edgardo Browne and Richard B. Firestone, ISBN: 0-471-84909-X, Sep. 1986, pp. 192-2 and 192-3.*

* cited by examiner

Primary Examiner—Chih-Cheng G Kao
(74) Attorney, Agent, or Firm—Armstrong Teasdale LLP

(57) ABSTRACT

A micro-radiation therapy apparatus includes an isotope-based micro-radiotherapy brachytherapy small animal irradiator useful for radiating a biological system, the irradiator having an external radiation source proximate the biological system comprising a collimated radiation beam. A method of effectively irradiating at least one cell in a biological system includes applying micro-radiation from an isotope-based micro-radiation small animal irradiator, the irradiator having an external radiation source proximate the biological system including a collimated radiation beam to a target cell of the biological system.

10 Claims, 32 Drawing Sheets

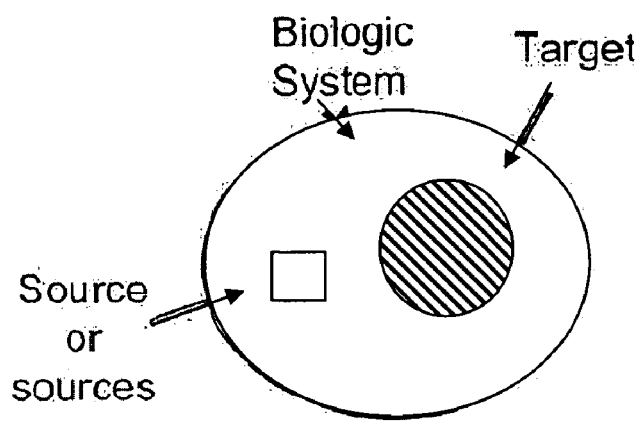
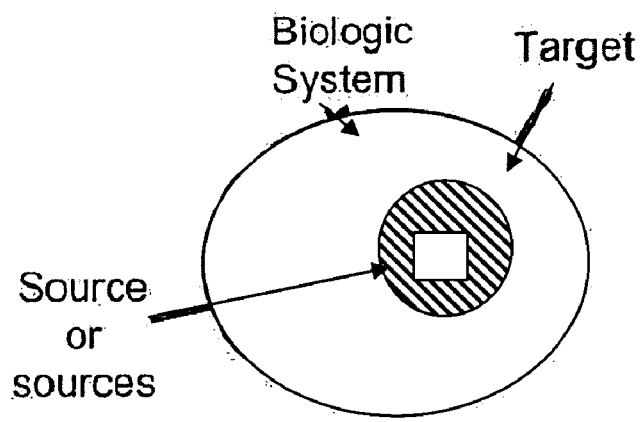
Figure 3B

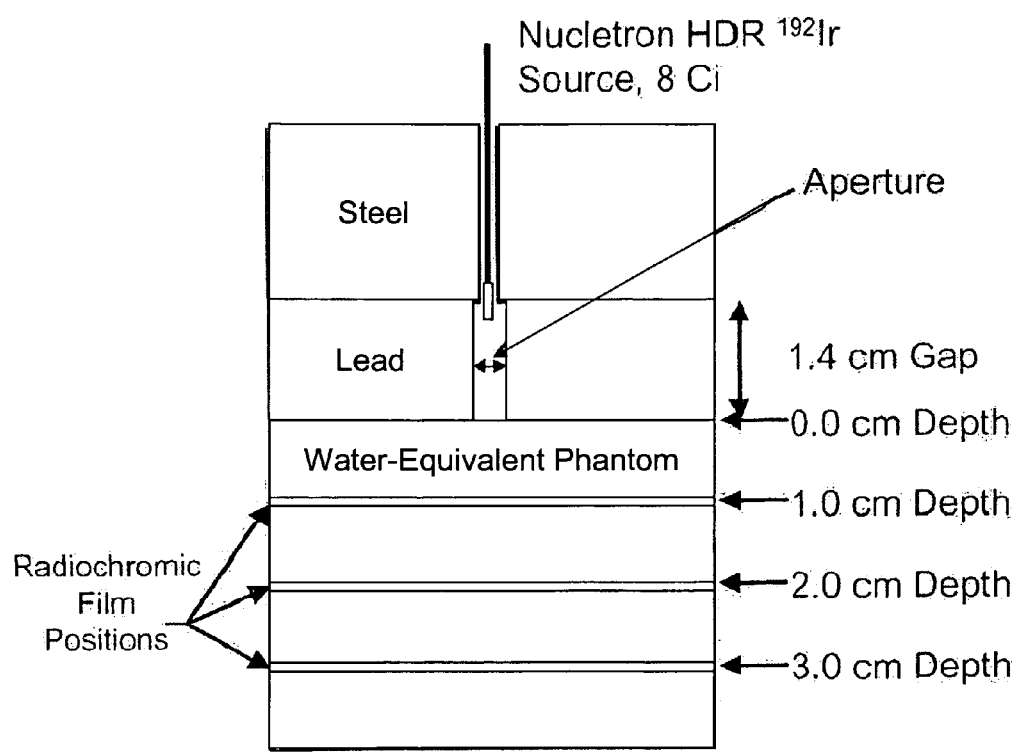
Figure 4   MICRO RADIATION THERAPY

MICRO RADIATION THERAPY

ENHANCED MICRO-RADIATION THERAPY AND A METHOD OF MICRO-IRRADIATING BIOLOGICAL SYSTEMS

CROSS REFERENCE TO RELATED APPLICATION

This application claims the benefit of U.S. provisional patent application 60/470,335 filed May 14, 2003 which is hereby incorporated by reference in its entirety.

FIELD OF THE INVENTION

This invention relates generally to micro-radiation therapy and a method of micro-irradiating small biological samples. In particular this invention relates to a micro-irradiation apparatus and use thereof to micro-irradiate biological (biologic) systems.

BACKGROUND OF THE INVENTION

Cancer (malignant neoplasm) is characterized by uncontrolled growth and spread of abnormal cells in a living animal and is one of the leading killer diseases of mankind in history. Each year in the U.S. more than a million people are diagnosed with cancer and half of those people so diagnosed will ultimately die from cancer. Cancer presents itself in human and non-human mammals and kills both.

Massive discovery efforts having been ongoing for years into discovering effective anti-cancer therapies including radiation therapy which can exterminate cancer in some instances and block the spread of cancer in some instances. In that regard, use of laboratory animal models (the use of small animals instead of humans for treatment including testing) and cell cultures are carried out (under accepted and approved protocol and standards) to determine radiation response of tumors and normal organs to an applied dose of radiation.

One present laboratory practice of irradiating animals employs ionizing radiation energy from teletherapy sources (for example, Cobalt-60) or generated x-rays. Such sources are sources which are commonly referred to as external beam radiation and are typically provided by an extended linear accelerator or radioactive source. External beam radiation and external beam radiation therapy is a form of radiation therapy in which the radiation is delivered by a machine pointed at the target area to be radiated and located external to that area, with the source relatively far from i.e. non-local to the patient, animal, or sample (80 cm-100 cm). Modern radiation therapy involving external beam sources include linear accelerators such as those produced by Varian Medical Systems 3100 Hansen Way, Palo Alto, Calif. 94304 USA (such as a Clinac 2300 medical linear accelerator).

During such radiation therapy, it is desired to predict or measure the radiation effect on tumorous tissue and normal organ tissue for the research to be effective. Further, it is desired to measure the extent, biological environmental progression and to measure physiologic quantities relating to the radiation response in small animal tumors, normal organs, or organ systems and so analytical measurements are required.

Presently in some instances radiation is used to therapeutically treat living non-human animals, usually of the order Rodentia, and pets or cattle having cancer, using equipment that is the same or similar to that used on humans. However, the smaller scale size of these animals compared to humans, for example rats and mice, makes the precise irradiation of these animals relatively difficult. Thus it is highly desired to have an apparatus and a method for effectively therapeutically treating animals that is more application selective as to the radiation impacted/targeted tissue locus.

Although currently extremity-implanted tumors can be homogeneously irradiated while shielding the rest of the animal, conformal techniques are desired for evaluating heterogeneous tumor irradiation response, in-situ tumor response, and normal organ response. The use of human-scaled equipment for delivery of conformal techniques remains unacceptable for treating small animals with irradiation.

More particularly in irradiating a small animal such as a mouse or rat, present radiation apparatus provide relatively undesirable large radiation beams to the target small animal. Therefore it is difficult to restrict the radiation distribution to the intended biological system target so that the distribution is well controlled. For example, the application of irradiation to target mouse tumors is difficult without also undesirably irradiating a substantial portion of a normal part of the mouse, causing undesired collateral radiation response effects on the non-desired tissue that obscure the response to the desired tissue tumor irradiation. Similar undesired complications are encountered when irradiating small animals for determining radiation response of their normal organs using present apparatus.

Progress has been more rapid in some areas of research than other areas. For example development of small animal imaging systems, such as micro-positron emission tomography (PET) and micro-computed tomography (CT) and micro-magnetic resonance imaging (MRI) has spawned a flurry of development of imaging agents to measure the extent, biological environment, progression, and response to diseases such as cancer, and to measure physiologic quantities of small animal normal organs or organ systems. However for radiation response, there has not been a similar development that allows one to take advantage of the available impressive imaging resolution. For some members of the small animal classification, such as cell cultures, accurate irradiation using a dose distribution with a controlled variation in intensity and spatial extent is virtually impossible with existing technology. The existing irradiators for small animals are unacceptably cumbersome and may not support the numerous radiation response tests needed.

BRIEF DESCRIPTION OF THE INVENTION

In one aspect, a method for applying conformal radiation to a small non-human living mammal (target mammal) is provided. The method comprises localizing accurately a radioactive source to the target mammal, obtaining a dose calculation for the target mammal optionally with a 3D dose calculation and/or a 3D image of the target mammal, and applying radiation conformally from the radioactive source to the target. In an aspect, the small non-human living mammal is a member of the order Rodentia.

In another aspect, the small non-human living mammal is a member of the order Lagomorpha (The order Lagomorpha comprises rabbits and hares (family Leporidae) and the small rodent like pikas (family Ochotonidae).

In another aspect, a method for applying radiation to a non-human living mammal (target mammal) comprises accurately localizing a radioactive source to the target mammal, obtaining a dose calculation optionally with a 3D dose calculation and/or a 3D image of the target mammal, and applying radiation to achieve an isotope-based brachytherapy using the radioactive source. In an aspect, the small non-human living mammal is four-legged mammal. In an aspect, the four-legged mammal is a rodent. In a further aspect, the rodent is selected from a rat, mouse, and a hamster.

In yet another aspect, a non-human mammal conformal radiation therapy system comprises an enclosure including a bore having a diameter less than about 30 centimeters, a radioactive radiation source, a manipulator positioned and configured to position the source substantially within the enclosure and at a distance between 1 cm and 15 centimeters from a non-human mammal and to retract the source to a source storage unit, and a collimator positioned to collimate radiation emitted from the source.

In another aspect, a non-human mammal conformal radiation therapy system comprises an enclosure including a bore having a diameter less than about 30 centimeters, a radioactive radiation source, an operably retractable mechanical apparatus positioned and configured to position the source substantially within the enclosure and at a distance between 1 centimeters and 15 centimeters from a non-human, and a collimator unit positioned to collimate radiation emitted from the source, wherein the operably retractable mechanical apparatus further configured to move the source within the collimator unit such that substantially no un-collimated radiation is emitted.

In an aspect, the manipulator is further configured to capably position the source substantially centered in the bore using a linear motion, the collimator rotatably mounted to rotate around the source when the source is positioned centered in the bore. As used herein the term manipulator refers to any means of manipulation apparatus including a retractable mechanical apparatus as well as a robotic arm.

In one aspect, a system wherein the retractable mechanical apparatus is further configured to position said source proximate an inner circumference of said bore using at least partially a circular motion.

A system further including a plurality of collimators positioned proximate the inner circumference is provided in one aspect, wherein the retractable mechanical apparatus further configured to position the source proximate any desired collimator.

A system further including a couch translatable in at least two dimensions within the bore and is configured to position the non-human mammal is herein provided.

A collimator useful to collimate a radiation beam in an isotope-based micro-radiotherapy irradiator apparatus includes an adjustable robotic arm supporting a metal shield apparatus housing a radioactive source projecting a radiation beam and having a selectable exit portal for radiation emanating from the radioactive source.

In an aspect, a micro-radiation therapy apparatus comprising an isotope-based micro-radiotherapy irradiator useful for irradiating a target biological system, the irradiator having a radiation source proximate the target biological system and comprises an adjustable or selectable collimated radiation beam. In an aspect, a collimator useful to collimate a radiation beam in an isotope-based micro-radiotherapy irradiator apparatus comprises a small gantry-mounted rotateable shield, where the gantry uses a circular support system that allows the shield to rotate about the target biological system and wherein the shield houses the radioactive source and has an exit portal for the radiation beam.

In an aspect of the present invention, a micro-radiation therapy apparatus comprises an isotope-based micro-radiotherapy irradiator useful for irradiating a target biological system, the irradiator having a radiation source proximate the target biological system and comprises an adjustable or selectable collimated radiation beam.

In another aspect, a collimator useful to collimate a radiation beam in an isotope-based micro-radiotherapy brachytherapy irradiator apparatus includes an adjustable robotic arm supporting a metal shield apparatus housing a radioactive source projecting a radiation beam and having a selectable exit portal for radiation emanating from the radioactive source.

In another aspect, a radiation collimator useful to collimate a radiation beam in an isotope-based micro-radiotherapy irradiator apparatus comprises a small gantry-mounted rotateable shield, where the gantry uses a circular support system that allows the shield to rotate about the target biological system and wherein the shield houses the radioactive source and has an exit portal for the radiation beam.

In an aspect, a method of effectively irradiating at least one cell in a target biological system includes applying micro-radiation from an isotope-based micro-radiation irradiator, the irradiator having an external radiation source proximate the biological system including a selectable collimated toxic radiation beam to a target cell or target cells of the biological system.

In an aspect, a method of effectively irradiating at least one cell in a single cell or multicell living biological system comprises applying radiation from a collimator projecting a radiation beam in a micro-radiation therapy apparatus wherein the collimator includes an adjustable robotic arm supporting a metal shield apparatus housing a radioactive source and an exit portal for radiation emanating from the radioactive source.

In an aspect, a method of effectively irradiating at least one cell in a single cell or multicell living biological system includes applying radiation from a collimator in a micro-radiation therapy apparatus wherein the apparatus includes an adjustable robotic arm supporting a metal shield apparatus housing a radioactive source projecting a radiation beam and having an exit portal for the radiation beam.

In an aspect, a method of effectively irradiating at least one cell in a single cell or multicell living biological system includes applying radiation from an adjustable collimator in a micro-radiation therapy apparatus wherein the irradiation is applied to a target cell or target cells using a dose distribution with a controlled variation in intensity.

In an aspect, a method of effectively irradiating at least one cell of a single cell or multicell living biological system comprises applying radiation from a collimator in a micro-radiation therapy apparatus wherein the irradiation is applied to a target cell or target cells using a dose distribution is mathematically modeled to allow for modeling and planning of the resulting dose distributions.

In an aspect, a method of treating neoplastic tissue by effectively irradiating at least one neoplastic cell in a single cell or multicell living biological system includes applying an effective amount of micro-radiation from an isotope-based micro-radiation irradiator, the irradiator having an external radiation source proximate the single cell or multicell living biological system includes effectively applying a collimated radiation beam to a target cell or target cells of the biological system whereby the neoplastic cell is made non-neoplastic or killed.

A radiation collimator configured to collimate a radiation beam in an isotope-based micro-radiotherapy irradiator apparatus, said radiation collimator comprising a gantry and rotateable shield mounted them, said gantry comprising a circular support system that allows said shield to rotate about a target biological system, said shield housing the radioactive source and having an exit portal for the radiation beam.

A radiation collimator configured to collimate a radiation beam in an isotope-based micro-radiotherapy irradiator apparatus, said radiation collimator comprising a rotateable shield that allows the radiation beam orientation to be selected and a moveable support system for the small animal that allows the target within the small animal to be aligned with the radiation beam.

A radiation collimator configured to collimate a radiation beam in an isotope-based micro-radiotherapy irradiator apparatus, said isotope being stored in a pig some distance from the irradiator with a mechanism to move the source into the collimator when the radiation beam is desired.

A method of effectively irradiating at least one cell in a target biological system comprises applying micro-radiation from an isotope-based micro-radiation brachytherapy irradiator, the irradiator having an external radiation source proximate the biological system comprising a selectable collimated radiation beam to a target cell of the biological system.

A method of effectively irradiating at least one cell in a biological system comprises applying radiation from a collimator projecting a radiation beam in a micro-radiation therapy apparatus wherein said collimator comprises an adjustable robotic arm supporting a metal shield apparatus housing a radioactive source and an exit portal for radiation emanating from the radioactive source.

A method of effectively irradiating at least one cell in a biological system comprises applying radiation from a collimator in a micro-radiation therapy apparatus wherein the apparatus comprises an adjustable robotic arm supporting a metal shield apparatus housing a radioactive source projecting a radiation beam and having an exit portal for the radiation beam.

A method of irradiating at least one cell in a biological system comprises applying radiation from an adjusting collimator in a micro-radiation therapy apparatus wherein the irradiation is applied to a target cell using a dose distribution with a controlled variation in intensity.

A method of irradiating at least one cell in a biological system comprises applying radiation from a collimator in a micro-radiation therapy apparatus wherein the irradiation is applied to a target cell using a dose distribution is mathematically modeled to allow for accurate modeling and planning of the resulting dose distributions.

BRIEF DESCRIPTION OF THE DRAWINGS

FIG. 3*b* depicts an aspect of this micro-radiation therapy using internal brachytherapy, both within and without a target.

FIGS. 4-17 depict geometry and test data results of a micro-radiation therapy setup (apparatus) to validate a Monte Carlo (MC) simulation of a brachytherapy source dose distribution apparatus.

DETAILED DESCRIPTION OF THE INVENTION

Herein described are methods and apparatus for enhanced medical care and comprehensive cancer services. Use of the herein described methods and apparatus provide for the treatment of small animals with irradiation using an enhanced apparatus.

Animal irradiation can be conducted either by kilo voltage irradiators or isotope-based irradiators. The kilo voltage irradiators are expensive and inflexible with respect to conformal animal irradiation. The isotope-based irradiators are non conformal and cannot be used as micro-radiation irradiators.

The present discovery may be understood more readily by reference to the following detailed description of non-limiting aspects of the discovery and the non-limiting Examples included herein.

It is to be understood that this invention is not limited to specific apparatus or to a specific method. It is also to be understood that the terminology used herein is for the purpose of describing aspects only and is not intended to be limiting. In addition, as used in the specification the singular forms "a," "an," and "the" include plural referents.

Figure 1:
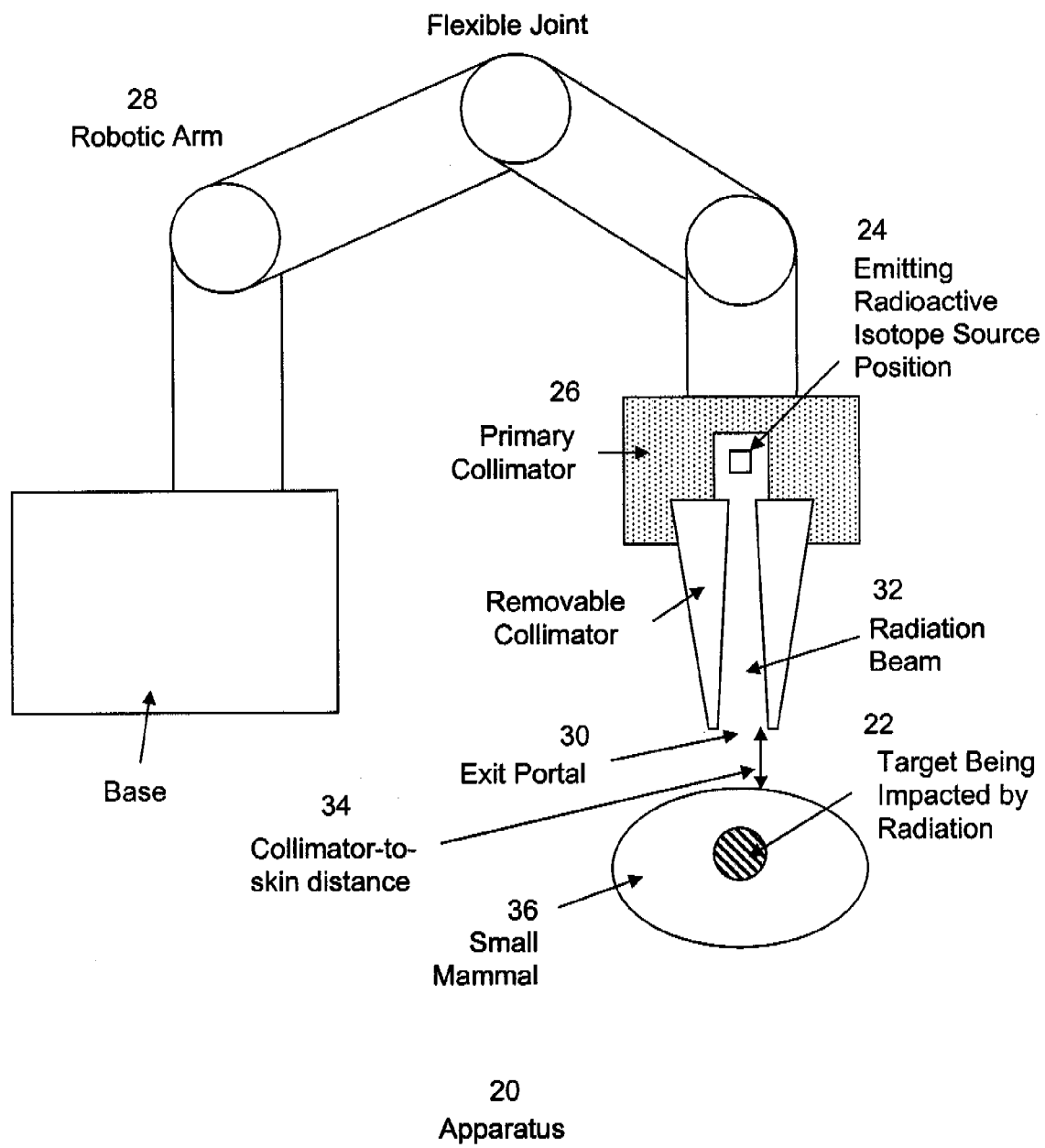
FIG. 1 depicts a micro-radiation therapy conformal irradiator in accordance with one embodiment.

In an aspect, and more particularly with respect to FIG. 1, novel isotope based micro-radiation device (apparatus) 20 delivers an effective targeted amount of desired ionizing radiation to a target biological system 22 using a radioactive isotope source 24 with greater accuracy than can be provided with current systems. Radioactive isotope source 24 is placed within a primary collimator 26 mounted to a computer-controlled commercial robotic arm 28. In one aspect, a series of precisely machined collimators is used to provide beam portal 30.

In an aspect, apparatus 20 uses a source to tumor distance range of about 6 cm to about 8 cm corresponding to a collimator to skin distance 34 and computer controlled robotic arm 28 is programmed to rotate beam 32 around small mammal 36 to deliver a conformal dose distribution. Robotic arm 28 is a single or multi-jointed arm comprising one or more sections of compatible suitable mechanical strength connected components. One of the robotic arm's functions is to move to a specified location or along a predetermined path so it can perform a task. In an aspect, motion consists of an articulated arm being actuated from a fixed pivot position.

In an aspect, small animal 36 is placed in an immobilization device (not shown) and prior to irradiation the target location is determined, either using imaging, by direct examination of the target specimen, or by indirect measurement with previously determined offset.

Fiducial markers (not shown) on the immobilization device (not shown) and the irradiation volume (not shown) are located to determine a center of rotation of irradiator apparatus 20. Since irradiator apparatus 20 is based on a robotic arm 28 collimator to skin distance 34 can be dynamically varied during rotation of the arm 28 to maximize the dose rate. Preliminary measurements (FIGS. 5-17) and confirmatory Monte Carlo simulations (FIGS. 6-17) using the BEAM computer code indicate that a dose rate at about 8 cm of approximately 200 cGy/min using a $^{192}$Ir source is feasible.

In an aspect, the illustrative useful apparatus depicted in FIG. 1 is useful to irradiate biological systems, including cells, cell cultures, and parts of or entire small animals. In an aspect, a useful biological system comprises a mouse or a rat. In an aspect, this invention provides a method of optimizing malignancy therapy.

In an aspect, articulated robotic arm 28 is a single or multi-compartment arm, which can be housed or automatically moved. Arm 28 and entire apparatus 20 is configurable to a desired size of a targeted use. In an aspect, a multi compartment arm comprises joined sections or components having flexible joints connecting them. Such joints comprise hinges, couplings, clevises, and the like.

As used herein, the term "micro-radiation" includes ionizing electromagnetic radiation and energy applied using therapeutic radiology which uses high-energy particles or waves, such as X rays or gamma rays, to focus damaging radiation on the region of a tumor, inflicting genetic damage that kills cancerous cells, or focus damaging radiation to cells or normal organs or organ systems, to study their response to ionizing radiation. X rays or gamma rays are a form of ionizing electromagnetic radiation. Gamma rays are produced by nuclear transitions and X-rays are produced by energy transitions due to accelerating electrons or due to orbital transitions by atomic electrons. Since it is possible for some electron transitions to be of higher energy than nuclear transition, there is an overlap between low energy gamma rays and high energy X-rays. Typically the energy of such high-energy waves is in the range from about 10 keV to about 2 MeV.

As used herein the term "accurately localizing" means positioning the animal within the irradiator in a position relative to the irradiator's pre-defined coordinate system, thereby positioning the target accurately with respect to the dose distribution. The irradiation dose will be determined by modeling the irradiator using a combination of direct measurements, Monte Carlo simulations of the radiation dose distributions, and mathematical models similar to those used in human conformal irradiation. The position of the target will be determined relative to the animal's anatomy using either visible and/or palpated and/or effectively measured using x rays. Once the target position has been determined, it will be positioned accurately with respect to the radiation beam as modeled with respect to the irradiator's coordinate system.

As used herein, the term "conformal radiation" means radiation obtained using a collimation system that reduced the high radiation area to a user-selected region of the animal, either through the use of 3-dimensional imaging and/or through the use of a predetermined relationship between the irradiated region and the animal's anatomy, either visible and/or palpated and/or measured using x-ray imaging.

As used herein, the term "multicell" includes a suspension or layer comprising multiple individual cells in a locale or in a sample or in an animal.

As used herein, the term "couch" includes a positioning place for the target animal which includes a surface of sufficient strength and suitable composition to effectively accommodate a target animal. The couch may be of any suitable configuration such as a flat surface or with fixtures suitable for effectively retaining the animal to the couch. Useful illustrative couches include the couch used for the microPET device fabricated by PETNET Pharmaceuticals, Knoxville, Tenn. USA.

In operation the animal is typically anesthetized for the duration of the radiation treatment using well known standard laboratory mouse anesthetic techniques.

When anesthetized the animal is placed on the couch and the radiation apparatus is placed in operation by turning on the electrical power and energizing the apparatus including the control system. When the radiation treatment is finished, the animal is removed from the couch where it has rested during radiation and is placed in a safe and suitable recovery area.

The dose distribution is computed by an algorithm specifically developed for the micro-radiation irradiator. The algorithm models the effects of the radioactive source size (geometric penumbra), the attenuation of the collimators, the distance from the source, the attenuation and scatter within the animal. The calculation will be conducted in three dimensions, with each point within the calculation having a unique distance from the source, depth within the animal, and distance and position away from the collimator.

In some cases, the dose calculation will be conducted in conjunction with a 3D image dataset of the animal (for example, from a microCT scanner). The dose distribution will be conducted using the 3D information contained within the dataset. The depths and distances of each calculation location (voxel) within the animal will be determined using the 3D image and this information will be used by the dose calculation algorithm to compute the dose within the animal. Typically, the target will be outlined within the 3D image and the dose within the target determined from the 3D dose calculation.

As used herein, the term "target" includes the portion of the animal that is to be irradiated and is typically the region that will be irradiated to the high dose. The target may be a cancerous lesion or a normal organ, depending on the objectives of the irradiation test.

In one aspect, apparatus 20 uses external brachytherapy to conformally irradiate cell cultures or small animal biological systems for research and therapeutic purposes. Useful illustrative forms of micro-radiation therapy encompassed by brachytherapy include intra-cavitary implant, interstitial implant, radium implant, cesium implant, high dose rate insertion and needle implant. In an aspect, an illustrative useful small animal biological system comprises a mouse or a rat.

In another aspect, the irradiator utilizes a radioactive emitting isotope as its energy source using brachytherapy to provide micro-radiation therapy. The radioactive isotope emits a sufficient supply of available energy in the form of gamma rays and/or X rays for directed and controlled bombardment of a target within a cell, a cell culture, or a small animal.

As used herein, the term "brachytherapy" includes radiation therapy in which radioactive material (radioisotopes) sealed in needles, seeds, wires, or other encapsulation, is placed directly into or near a tumor, cell culture, normal organ or organ system. Further, as used herein, the term "brachytherapy" encompasses the use of radioactive sources that are inside, in contact with, or immediately proximate to a biological system. As used herein, sources outside the biological system but nearby, touching and nontouching but closely proximate to the biological system are considered as being within the meaning of the term brachytherapy as used herein. Typically brachytherapy is radiation therapy given at a short distance from the target and it is localized, proximate, and precise.

The herein described methods and apparatus are useful with the use of radioactive prostate seed implants used to treat early stage prostate cancer in male mammal patients. In an aspect, small, such as tiny radioactive seeds are implanted into the prostate gland. The low level radiation is distributed continuously by each seed over a period of several months.

As used herein the term "sample" includes a representative sample such as a sufficient quantity of a living animal which adequate represents the animal for purposes of this discovery.

Radiation, as used herein, includes radioactivity from available emitting radioactive sources such as emitting cesium, gold, iodine, iridium and palladium isotopes which are placed directly into the effected tissues (intestinal) or body cavities (intracavity) in an invasive medical procedure. In an aspect, both high and low dose rate implants are employed. In an aspect, both temporary and permanent brachytherapy may be employed in practicing this invention.

In an aspect, an implant is used which comprises an interstitial seed implantation alone or in conjunction with external radiation as an adjunct. In an aspect, the implant is surgically placed within the animal.

As used herein the term "biological systems" include those biological systems which contain at least one living cell as well as multicell systems, and include small animals in the orders of Rodentia and Lagomorpha such as mice and rats.

As used herein, the term "cells" include those cellular systems having cells which comprise biological elements enclosed in a cell membrane that allows molecules to pass out of it and allows other molecules in. In an aspect, a cell includes each one of algae, fungi, and bacteria.

As used herein the term "isotope" (sometimes referred to as radioisotopes or radionuclides) includes man-made elements produced in a neutron flux field and in an aspect, include those emitting isotopes which are available from University of Missouri, Columbia, Mo. 65211 USA nuclear research reactor facility. A nonlimiting listing of useful radioactive emitting isotopes is found in the book Table of Radioactive Isotopes, Edgar do Browne, Richard B. Firestone, ISBM: -471-84909-X, Hardcover, 1056 pages, September, 1986.

Commercially available sources for isotope products include Isotope Products Laboratories, 1800 N. Keystone St., Burbank, Calif., and Atlantic Nuclear Corporation, 1020 Turnpike St. unit 9, Canton, Mass.

As used herein, the term "collimator" includes a functional radiation beam director or shield which comprises a device made of a highly absorbing material such as lead which directs or selects X- or gamma-rays along a particular direction and whose aperture may be either fixed, adjustable and manipulable.

In an aspect, a collimator comprises a moveable gantry mounted shield, where the gantry uses a circular support system that allows the shield to rotate under direction and control about the biological system to provide conformed therapy. In an aspect, the gantry is a small gantry. In an aspect, the shield houses the radioactive source and has an exit portal for the radiation beam to proceed on its path from its emitting radioactive isotope, through the collimator and onward to the target cell. In an aspect, a collimator comprises a fixed, mounted radiation shield, where the biological sample is moved and/or rotated to allow the beam to enter in user-specified angles and locations.

As used herein, the term "gantry" includes a support mechanism for the source and collimator that allows manipulation necessary to aim the radiation beam at the target.

Illustratively useful radioactive sources include those sources which provide a competent continuing supply of radioactivity including but not limited to $^{192}$Ir.

In an aspect, the exit portal of the collimator comprises a fixed or adjustable suitably sized opening.

In an aspect, a collimator comprises a moveable flexible single or multi-component robotic arm supporting a metal shield apparatus that houses a radioactive source and has an exit portal for the radiation beam. The use of a robotic arm allows for accurate and flexible application of the radiation. In an aspect, the parts of the multi-component arm is effectively connected together and functions as a unit. This provides for the capability of effective three dimension movement simulating multi-directional movement of a living human arm.

In one aspect of the invention, an emitting radioactive source is inserted into the biological sample, for example through the use of inserted catheters or directly implanted into the biological sample.

In an aspect, the micro-radiation therapy device utilizes a radioactive source selected from the group consisting of an x-ray, gamma ray, alpha, positron, and/or beta source as appropriate for the irradiation application. Typically useful sources for the x-rays are not limited to $^{192}$Ir.

In an aspect, the amount of emitted radioactivity desired to impact on the target is an effective functional amount and is that amount which upon impact with the target produces at least a discernible impact or result. In an aspect, the amount of radioactivity successfully impacted to the target is a measurable effective amount. In an aspect, cancer cells are altered by impacting toxic radiation on the target to render the cancer cells incapable of continued unlimited propagation, i.e. cancer cells are killed.

In an aspect, the form of brachytherapy given is supplied by the surgical invasive placement of radioactive seeds such as Iodine-125 within an animal. In an aspect, these are tiny pellets which are about the size of grains of rice. Such as typically injected into the animal with a medically approved needle like device.

In an aspect, the form of brachytherapy given includes a high dose rate ("HDR") unit wherein long very thin insertion catheters (or tubes) are placed into neoplastic tissues through the small animal's skin using ultrasound guidance in a surgical invasive procedure. These placements are referred to as afterloading catheters which are held tightly in place through a template which is temporarily sutured to the small animal's skin or other tissue. Generally this type of brachytherapy known as HDR, which involves radiation therapy in which the radiation source is removed from an animal patient between radiation treatments, the radiation treatments taking place when the source is proximate to in the animal.

In an aspect, a target of the radiation provided by this apparatus and method comprises at least one living cell in a culture. In an aspect, the target is a selective target, i.e., a target which is either a tumor cell or normal tissue cell or both types of cells. This invention provides an enhanced method of delivering emitted radiation to the desired target.

As used herein, the term "tumor" includes an abnormal uncontrolled growth of tissue which may be either malignant or benign and which has resulted from mitotic activity.

As used herein, the term "normal tissue" means tissue present in a small animal which performs a biological function and is biologically useful in some regard in that small animal to the animal and is not tumorous or neoplastic.

As used herein, the term "small animal" includes those members of the order Rodentia which includes mice, rats, hamsters, and guinea pigs, which are commonly kept as human pets. Mice includes transgenic mice, hybrid mice, and all other species in the suborder myomorpha, jerboas, and dormice. Rodentia includes beavers, muskrats, porcupines, woodchucks, chipmunks, squirrels, prairie dogs, marmots, chinchillas, voles, lemmings. Other small animals include chickens, ducks, fowl, squirrels, chipmunks, rodents, mice, rats, porcine, canine, and feline. It is to be understood that the description hereof with respect to a mouse is likewise applicable to small animals including members of the orders Rodentia and Lagomorpha. As used herein, the term "rat" includes rodent, gnawer, gnawing animal, common domestic rat, transgenic rat, black rat, roof rat, brown rat, bandicot rat, jerboa rat, rice rat, sand rat and gerbil, wood rat, pack rat, Polynesian rat, kangaroo rat and in general members of the Order Rattus.

As used herein, the term "biological system" includes a living biological system including Rodential and Lagedofinia comprising at least one cell. In an aspect, the at least one cell comprises a single cell within a culture or animal.

In an aspect, the radiation applied to the target is conformal radiation applied via conformal radiation therapy.

As used herein, the term "conformal radiation therapy" comprises a radiation therapy that utilizes a computation such as a computer using computational software to create a 3-dimensional picture (image) of the tumor or cancer target locus and normal organs to an operator of this novel apparatus so that the multiple radiation beams can be shaped exactly (conform) to the contour of the locus treatment area.

As used herein, the term "small animal irradiation" includes radiation applied to a small animal as a treatment including research and therapeutic applications. As used herein the term "applied" means delivered to and impacted upon. The target has received as it has been contacted by radiation emitted by the emitting radiation source. The treatments herein encompass external beam radiation and brachytherapy.

Generally the amount of radiation applied to a target cell is at least one of a controlled, therapeutic, prescribed, modeled and/or regulated functional amount. In an aspect, the intent of application of the radiation is generally to produce a therapeutic effect on a target cell within target tissue.

As used herein, the term "therapeutic" means that the subject or target of the applied radiation has shown or provided an effect which is deemed biologically beneficial to the subject or target.

The isotope-based micro-radiation brachytherapy irradiator of the present invention provides a well-defined narrow treatment radiation beam with useful depth-dose and dose-rate characteristics. The depth dose falloff can range from 5% per centimeter to 400% per centimeter. The dose-rate can vary from 1 cGy per minute to 1000 cGy per minute or greater.

Typical depth-dose characteristics include and are not limited to the amount of radiation reaching internal tissues and quantified as a function of depth in the tissue. The depth dose typically decreases exponentially with depth and inversely proportional to the square of the distance from the source.

Typical dose-rate characteristics include and are not limited to the intensity of radiation, or amount of radiation per unit time reaching a point. This is typically affected by the distance of the point from the source, the distance of the point off the collimator central axis, and the depth in tissue of the point.

In an aspect, the irradiator is a multi-collimator such as one having two collimators, a primary collimator and a secondary collimator.

The purpose of the primary collimator is to contain the radiation that has been emitted from source that cannot or will not be used for irradiating a target specimen.

The purpose of the secondary collimator is to limit the radiation beam to a user-selected size, typically but not limited to rectangular or cylindrical shapes and further focus on the target so that it is directed to the target. In one embodiment, the primary and secondary collimators are combined in a single unit.

In an aspect, the source of radiation, such as an emitting isotope is positioned in a primary collimator, which will in turn be mounted on a computer controlled robotic arm.

In an aspect, the robotic arm (a manipulator) is infinitively manipulable in multi-directions and in an aspect, is manipulated, i.e., controlled or positioned by action of the output signal of an associated operational computer. Such optional manipulation allows the robotic arm to provide a conformational delivery of the radiation to a selected target. In an aspect, a computer is equipped with software having the capability to provide operating directive output to the robotic arm from the computer which responds to the computer output and effectively moves in the desired direction(s) in response to the associated computer robotic arm directing output. In an aspect, the robotic arm houses a collimator.

In an aspect, the computer is programmed with software and the computers uses its software to receive an input signal indicative of the position of the robotic arm and to correspondingly generate an output command signal thereto which is intended to place the arm in a desired controlled predetermined orientation and position relative to the target. A transducer or system thereof having suitable transducing operable capability between an operating instructed computer and a robotic arm is employed to provide instructional movement signals to the robotic arm.

In an aspect, the arm is infinitively manipulatable by appropriate instructive communicative output signal transmitted thereto from the computer. Any effective computer may be employed to manipulate the moveable robotic arm.

Useful suitable moveable, controllable and infinitely adjustable robotic arms and hands are available commercially and generally comprise a tactile array sensor located on the right half of its gripping mechanism sends information to the robot's control computer about the pressure the robotic hand exerts; given this information, the control computer instructs the robotic hand to loosen, tighten, or maintain the current gripping force. This feedback loop repeats semi-continuously or continuously, enabling the robotic arm to stay in or vary from various desired positions.

It is understood that various components of the novel micro-radiation apparatus as described herein are operable connected in a manner and way such that the apparatus and method are operable and useful and produce the desired result of radiation treatment In an aspect, the primary and secondary collimators are machined either in-house or using a contract machine shop. In an aspect, the secondary collimators are supported by the primary collimator, which in turn is supported by the robotic arm. The robotic arm may be purchased commercially and the make and model depends on the use of the device (for example, the size of animals it is intended to irradiate). Alternatively, if the gantry or fixed beam is used, the hardware is machined either in-house or using a contract machine shop. The computers are purchased commercially (for example, from Dell Corporation, Houston, Tex.). In an aspect, the radiation source is produced by University of Missouri research reactor Columbia, Mo. USA.

In an aspect, the computer is connected to a controller that operates the arm. The arm is connected to the collimator which houses the radioactive source. The collimator consists of primary and secondary collimators. The arm is used to aim the collimated beam at the target during the radiation procedure.

In an aspect, the device is used to irradiate the biological sample. First the biological sample is attached to the irradiator system. This may be done using a fabricated support system such as a custom fabricated support system. The target is defined. The target is a tumor, part of a tumor, a normal organ, normal organ system, part of a normal organ, or a single or collection of cells within a cell culture. The target may be identified on a computed tomography scan, a positron tomography scan, or other imaging modality, or may be identified using a coordinate system inherent to the irradiator, or may be determined by directly contacting the target using a commercial 3D digitizer. A simulation of the radiation dose distribution is calculated. This may be a custom-3D dose distribution prepared for this specific test setup, or may be a pre-calculated dose distribution based on known target and biological sample geometry.

The robotic arm is programmed (it has its own software and computer operator system), given the irradiators previously determined radiation properties (such as beam intensity) to deliver the predetermined dose distribution. The robotic arm will then be instructed to irradiate the sample and the sample is removed from the unit. In an aspect, the unit is turned on and radiation is applied to the target. After a sufficient time, the unit is turned off and the target is analyzed for radiation effect. Appropriate safeguards are employed to prevent excessive radiation application and exposure.

In an aspect, the primary collimator comprises a high density, high atomic number metal such as 21 or higher. Computer simulations such as MC, will determine the optimal material for a specific radioactive source type and intensity. Similarly, the removable collimator is fabricated using high density, high atomic number metal. The robotic arm is made using the materials selected by the manufacturer, and the biological sample support hardware is fabricated using low atomic number, low density materials, again optimized as a function of the radioactive source. For example, lead may be used where high density, high atomic number materials are required, while polystyrene may be used where low density, low atomic number materials are required.

In an aspect, the size of the apparatus is sized such that it reasonably accommodates the biologic system to be appropriately irradiated. It is understood that generally a feedback signal loop is present and operating on the opening and manipulation of both collimators such that the beam is appropriately and selectively directed to the target cell to be irradiated. The amount of radiation is in the range from about 0.001 Gy to about 200 Gy and generally from about 0.1 Gy to about 20 Gy.

Typically the weight of the biological system or samples thereof is in the range from a weight of at least one living cell to about 500 kg and generally from about 1 gm to about 10 kg.

As used herein, the term "seeding" includes the placement of radioactive seeds or pellets (capsules) which emit relatively low level radiation into a target tissue so that such target (generally tumorous) tissue is destroyed.

Advantageously the collimators herein result in the increased delivery of dose to target volumes while reducing dose to nearby non-target normal tissue and critical structures. The collimators in one embodiment are made of a highly absorbing material such as lead or tungsten which directs X- or gamma-rays along a particular direction.

In an aspect, data analysis and optimization of the radiation dose, is conducted using software written in commercial programming environments, such as MATLAB, or in programming environments, such as the C programming language. MATLAB is a technical computing software available from The MathWorks Headquarters, 3 Apple Hill Drive, Natick, Mass. 01760-2098

FIG. 1 depicts a micro-radiation therapy conformal irradiator in accordance with one embodiment of the present invention the micro-radiation therapy irradiator has a removable and/or changeable collimator, source position, and/or permanent (primary) collimator.

Figure 2:
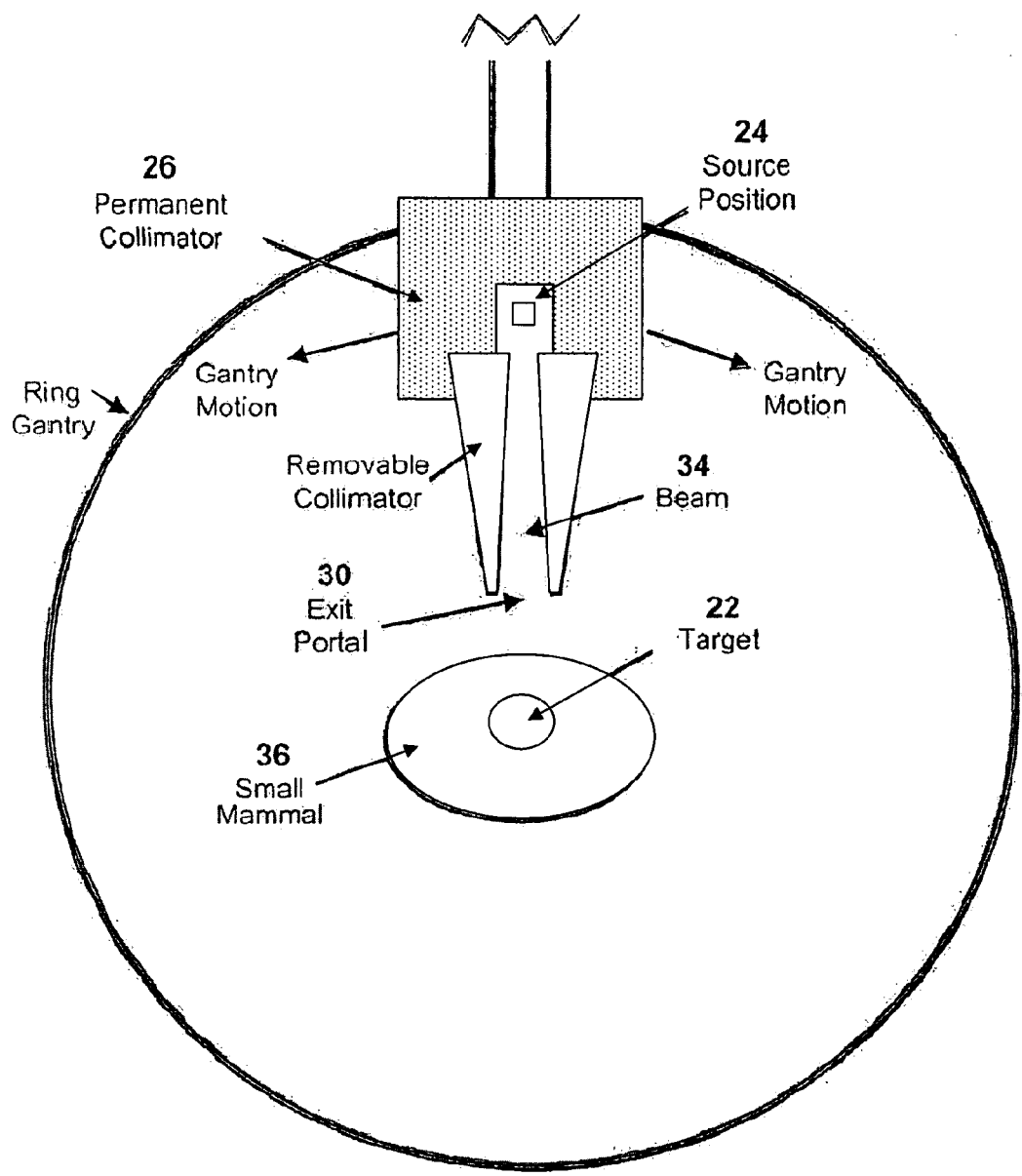
FIG. 2 depicts the irradiator shown in FIG. 1 operably configured for having rotational optionally continual gantry motion.

FIG. 2 depicts the irradiator shown in FIG. 1 operably configured for having rotational optionally continual gantry motion.

Figure 3:
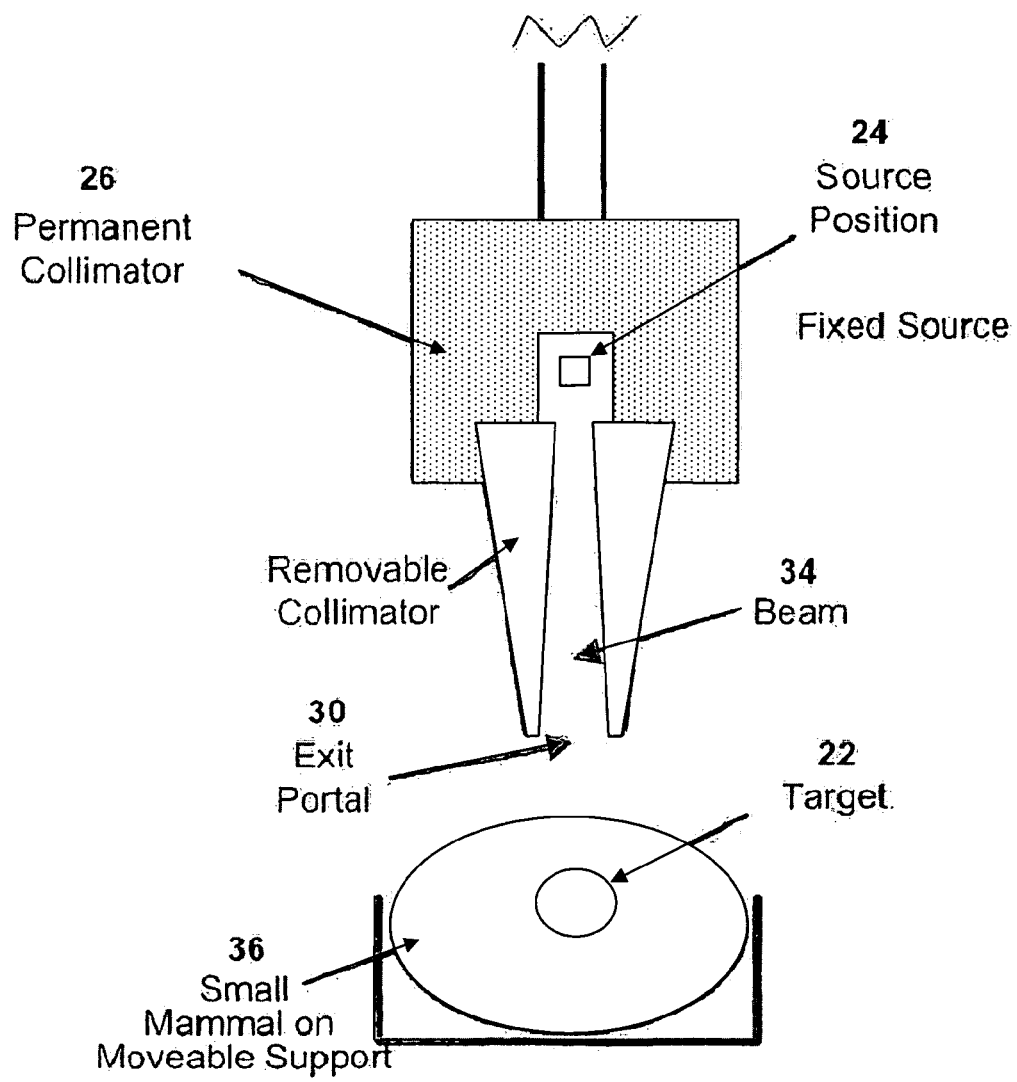
FIG. 3 depicts the irradiator shown in FIG. 1 including a target that is suitably positioned on a movable support.

FIG. 3 depicts the irradiator shown in FIG. 1 including a target that is suitably positioned on a movable support.

Figure 3A:
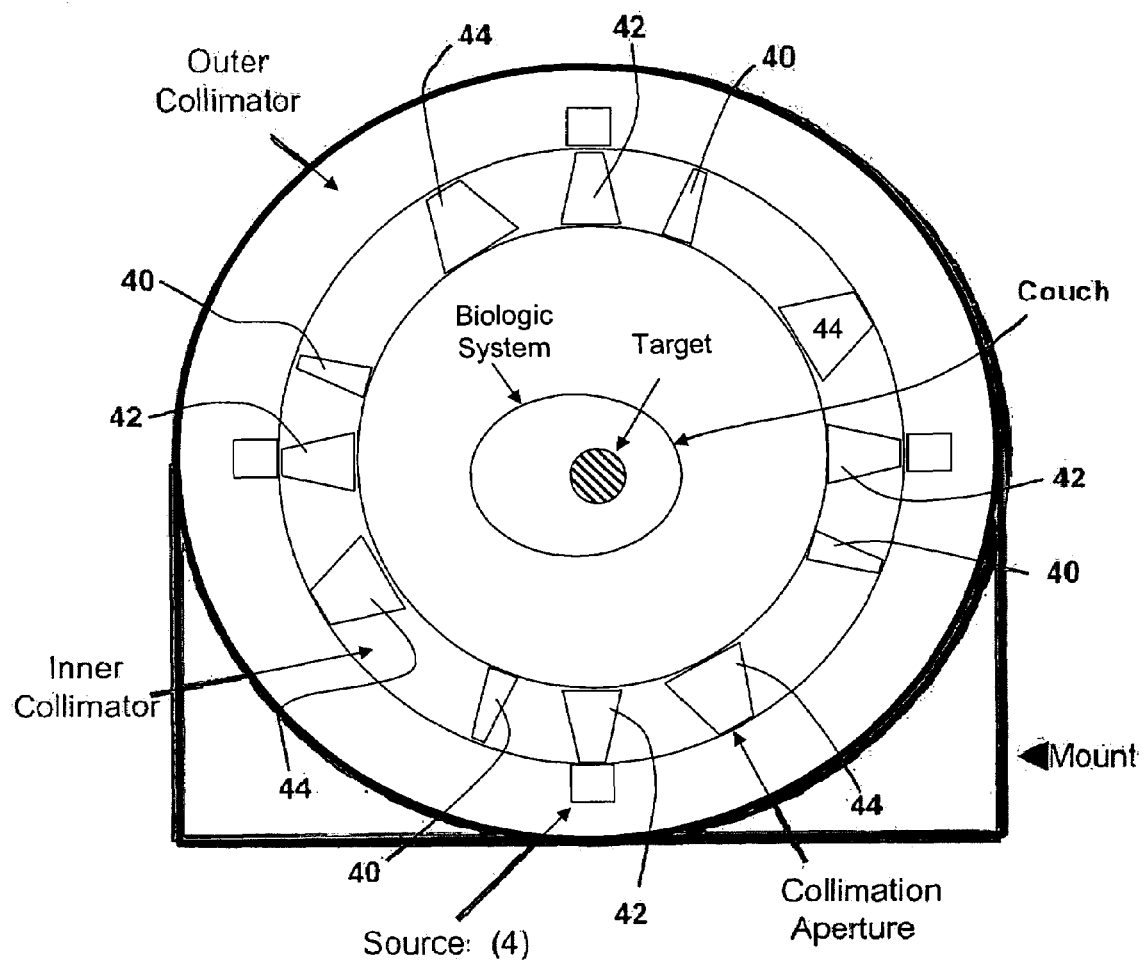
FIG. 3*a* depicts an aspect of micro-radiation therapy wherein multiple radiation sources are used to provide micro-radiation therapy beams to the target.

FIG. 3a depicts an aspect of micro-radiation therapy wherein multiple radiation sources are used to provide micro-radiation therapy beams to the target. For example, a multi-collimator apparatus is shown having outer and inner collimators and fabricated using a high atomic number material to adequately shield the unirradiated regions of the biological system and support personnel. Multiple radiation sources are shown in the outer collimator. The number of radiation sources can be from 1 to 300, for example, 1, 2, 3, 4, 5, etc. FIG. 3a depicts the case where four radiation sources are employed. In the instance of multi radiation sources, one or more of the radiation sources are of different or the same radiation sources and may also independently vary as to the emission strength of the radioactive source. The collimators are machined by a machine shop and are mounted to the floor or a suitable table using the mount. The inner collimator has selectable or adjustable collimation apertures which are selected by rotating either the inner or outer collimator or both the inner or outer collimator, or by moving aperture components that provide the user-specified aperture size. Radiation reaches the target when the collimator aperture is aligned with a source. The number of collimator apertures is from 1 to 300, for example, 1, 2, 3, 4, 5, 6, etc. The figure depicts the example where three different collimator aperture sizes are available for use. For example, a first plurality of apertures 40 are a first size, while a second plurality of apertures 42 are a second size larger than the first size, and a third plurality of apertures 44 are a third size larger than the second size. During the therapy, the sources may be moved such as by rotating the outer collimator to deliver the desired conformal dose distribution. If desired one radiation source may be aligned with one collimator to deliver an effective amount of radiation to the target. If desired two or more radiation sources may be aligned with two or more corresponding collimation apertures to deliver an effective amount of radiation to a target. If desired the radiation may be applied in one or more treatments to the subject or target receiving the radiation in accordance with the herein described methods and apparatus.

FIG. 3b depicts an aspect of this micro-radiation therapy using internal brachytherapy, both within and without a target.

FIGS. 4-17 depict geometry and test data results of a micro-radiation therapy setup (apparatus) to validate a Monte Carlo (MC) simulation of a micro-radiation brachytherapy source dose distribution apparatus.

Figure 5:
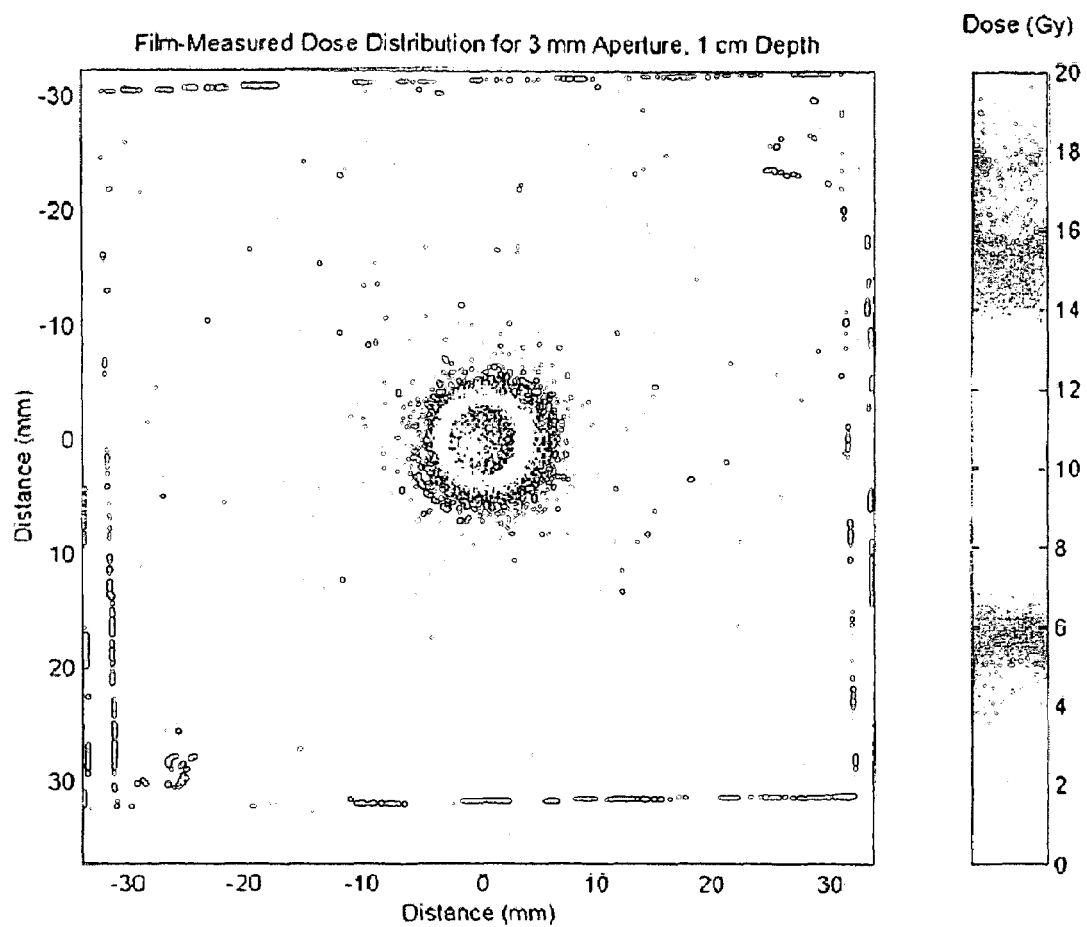
Figure 6:
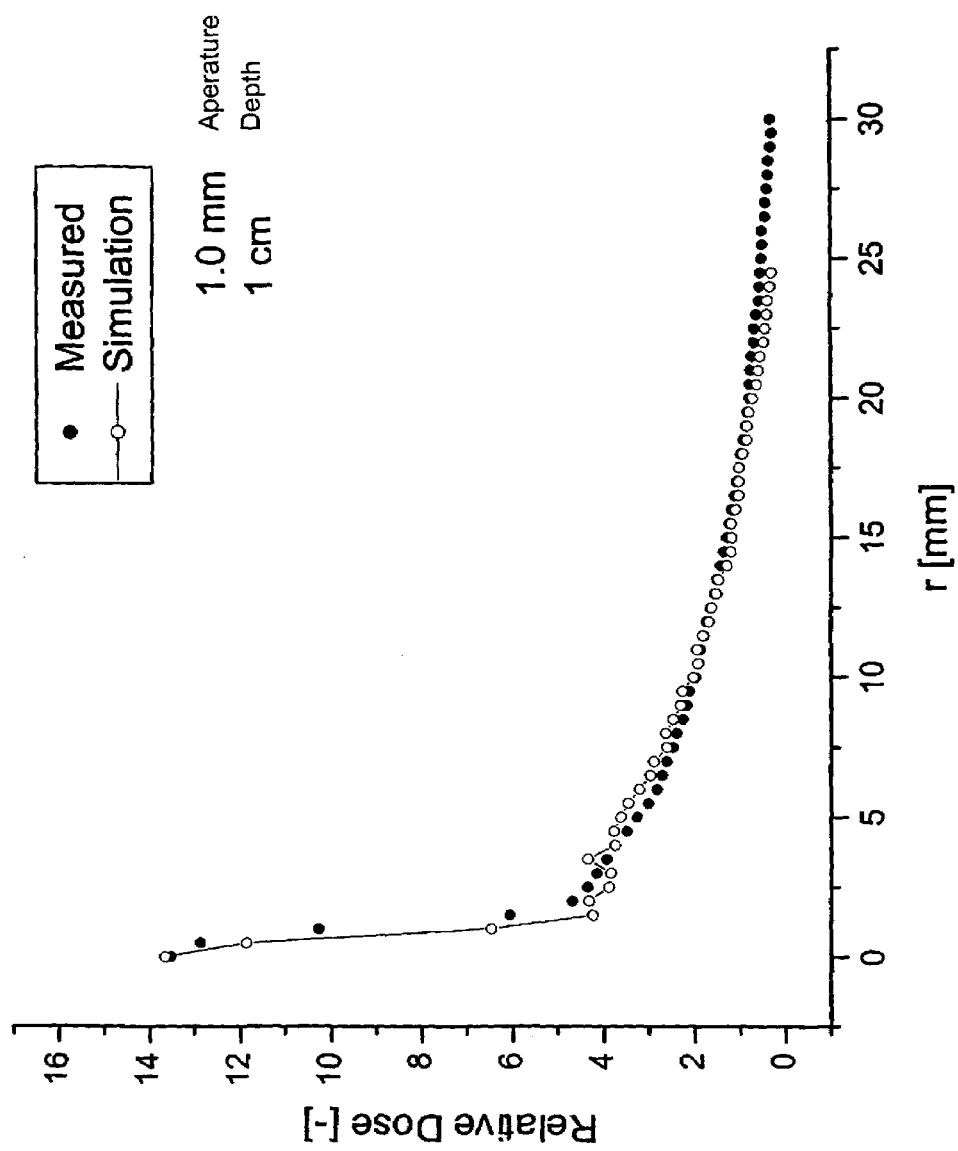
Figure 7:
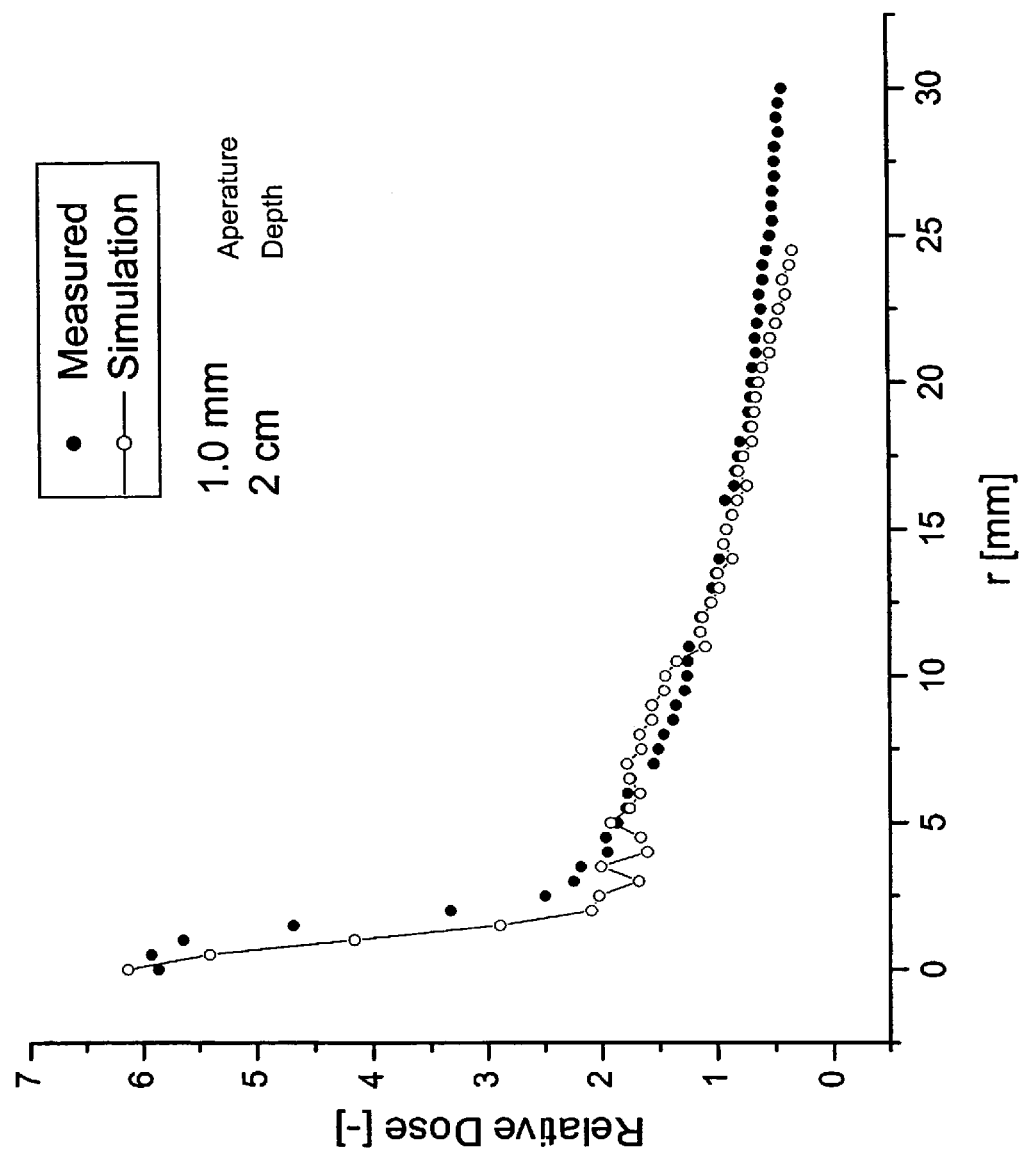
Figure 8:
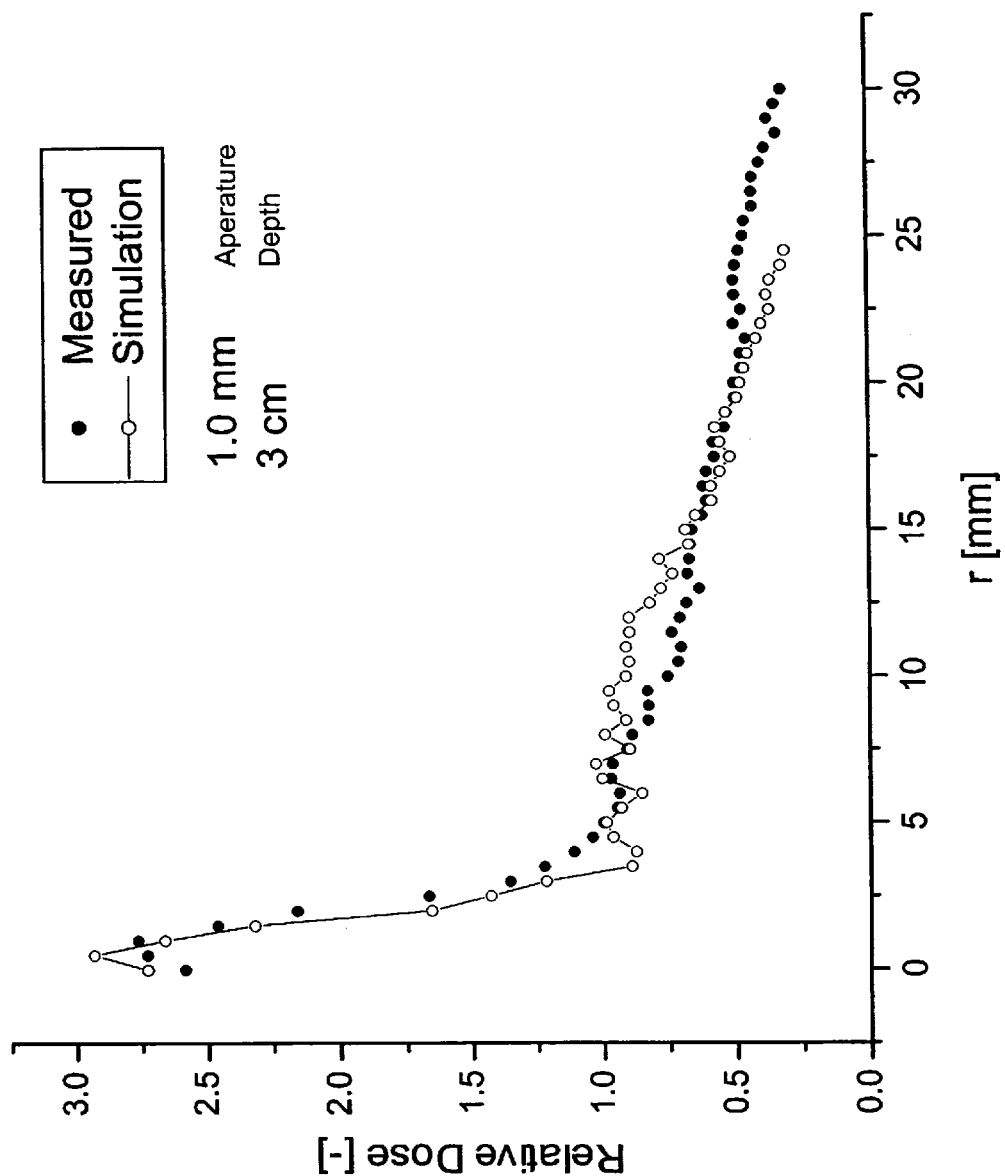
Figure 9:
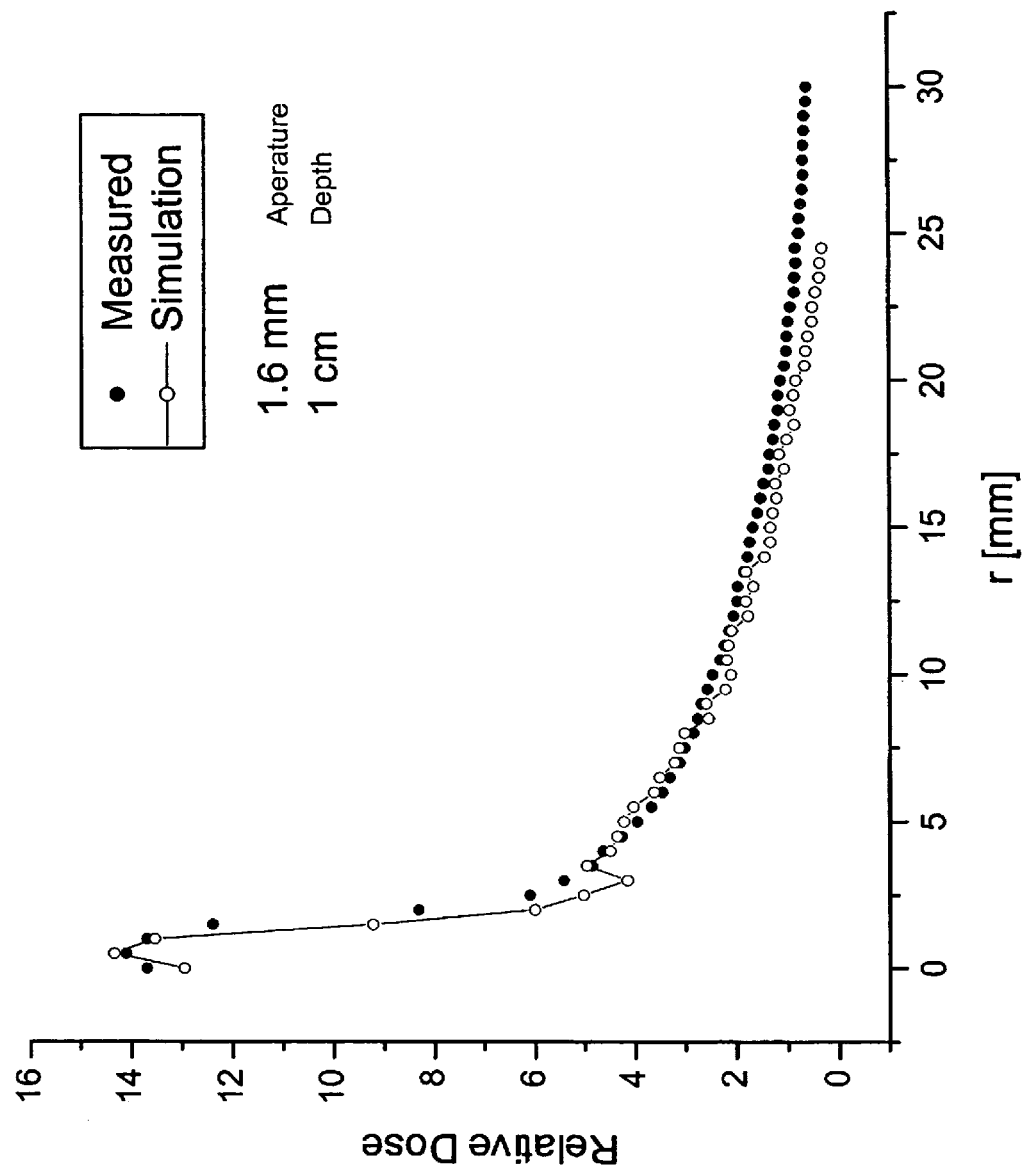
Figure 10:
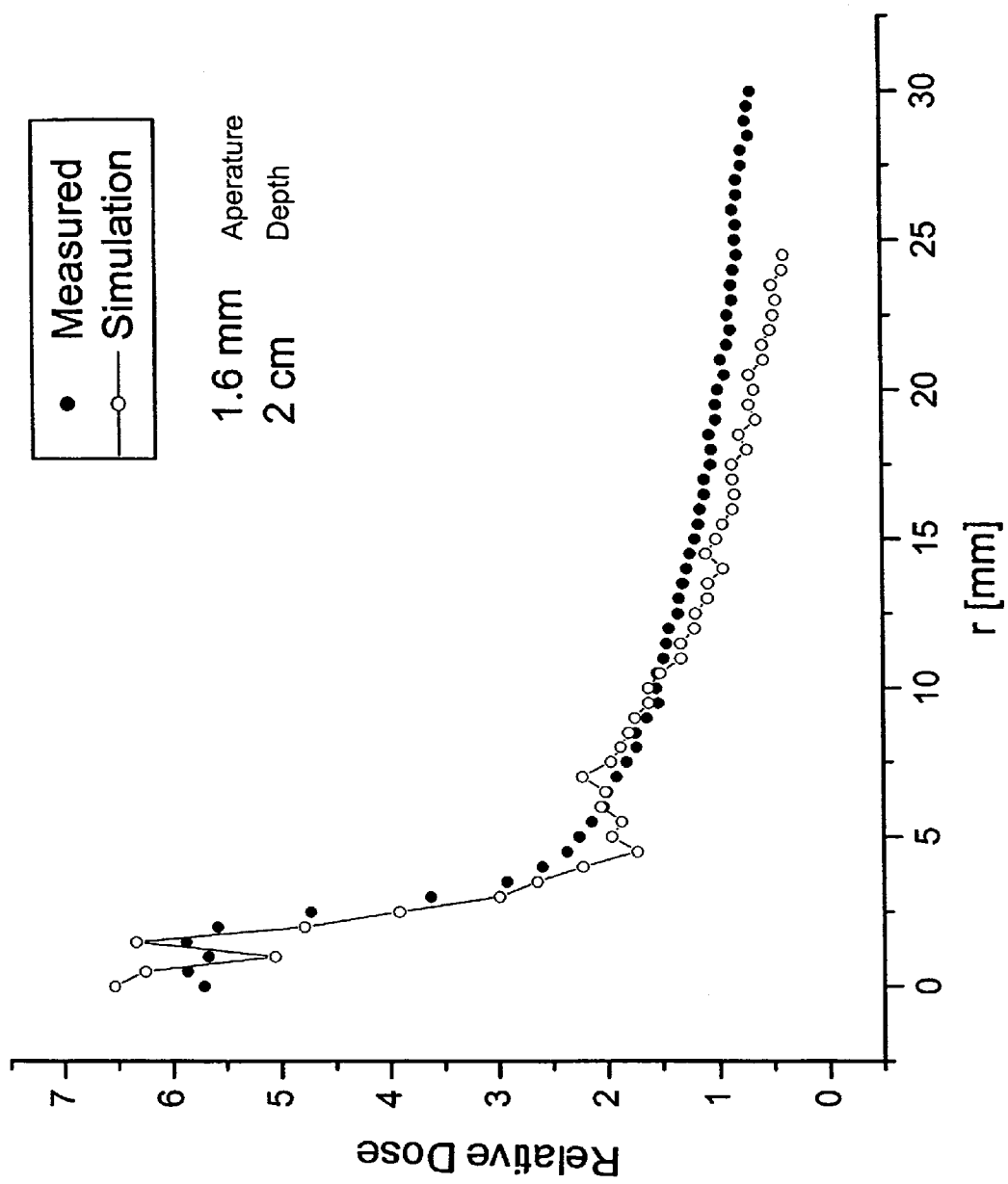
Figure 11:
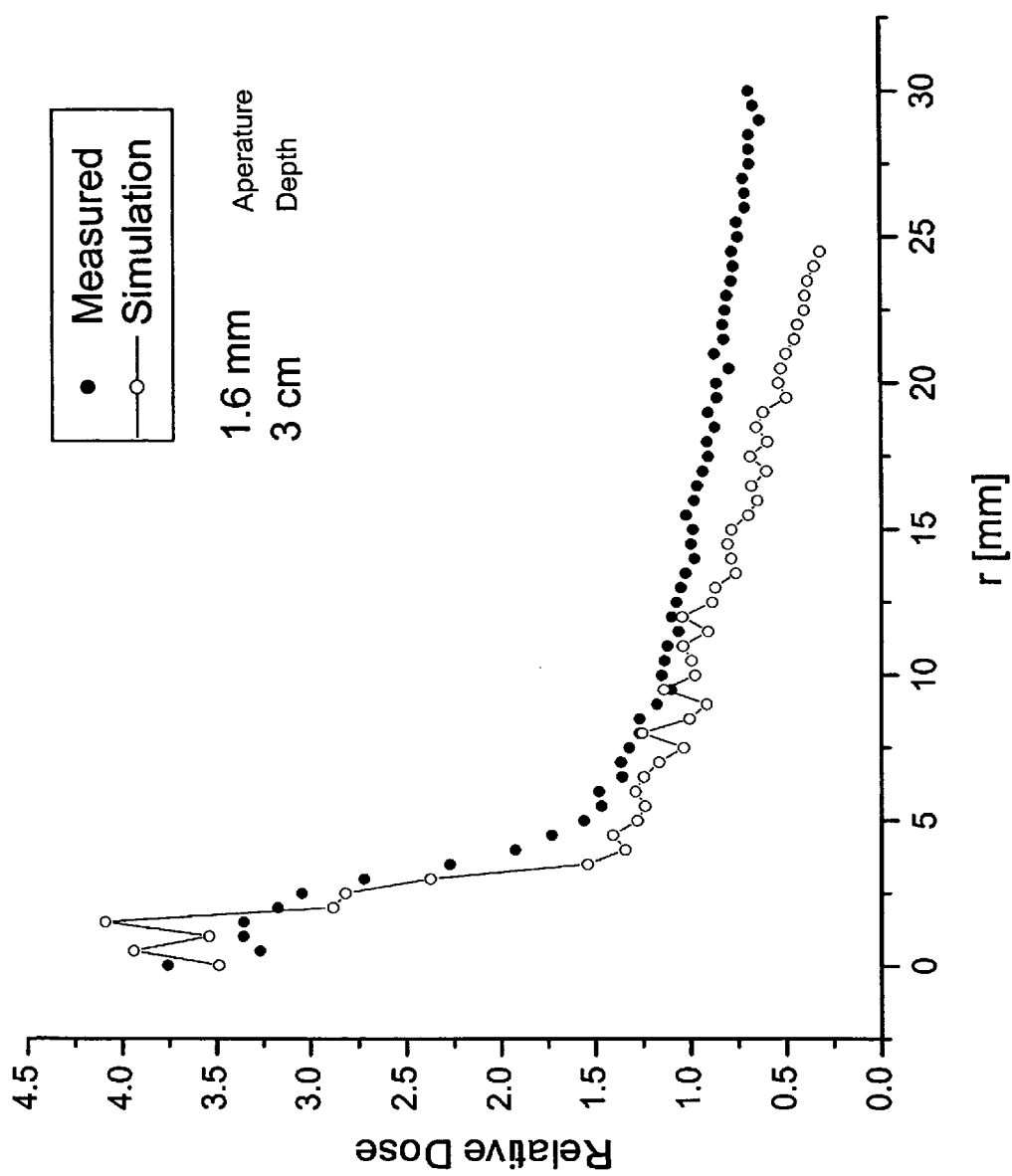
Figure 12:
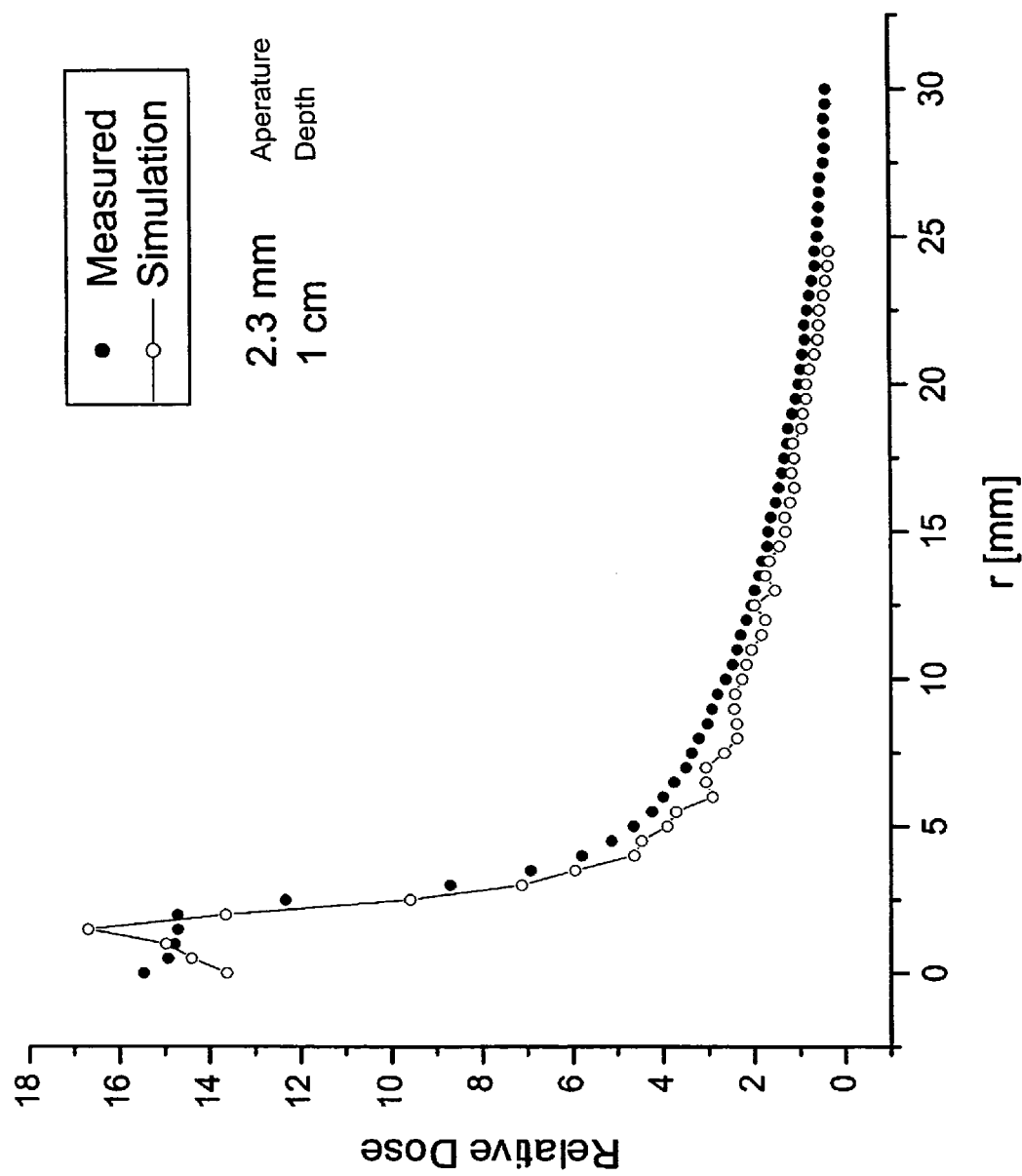
Figure 13:
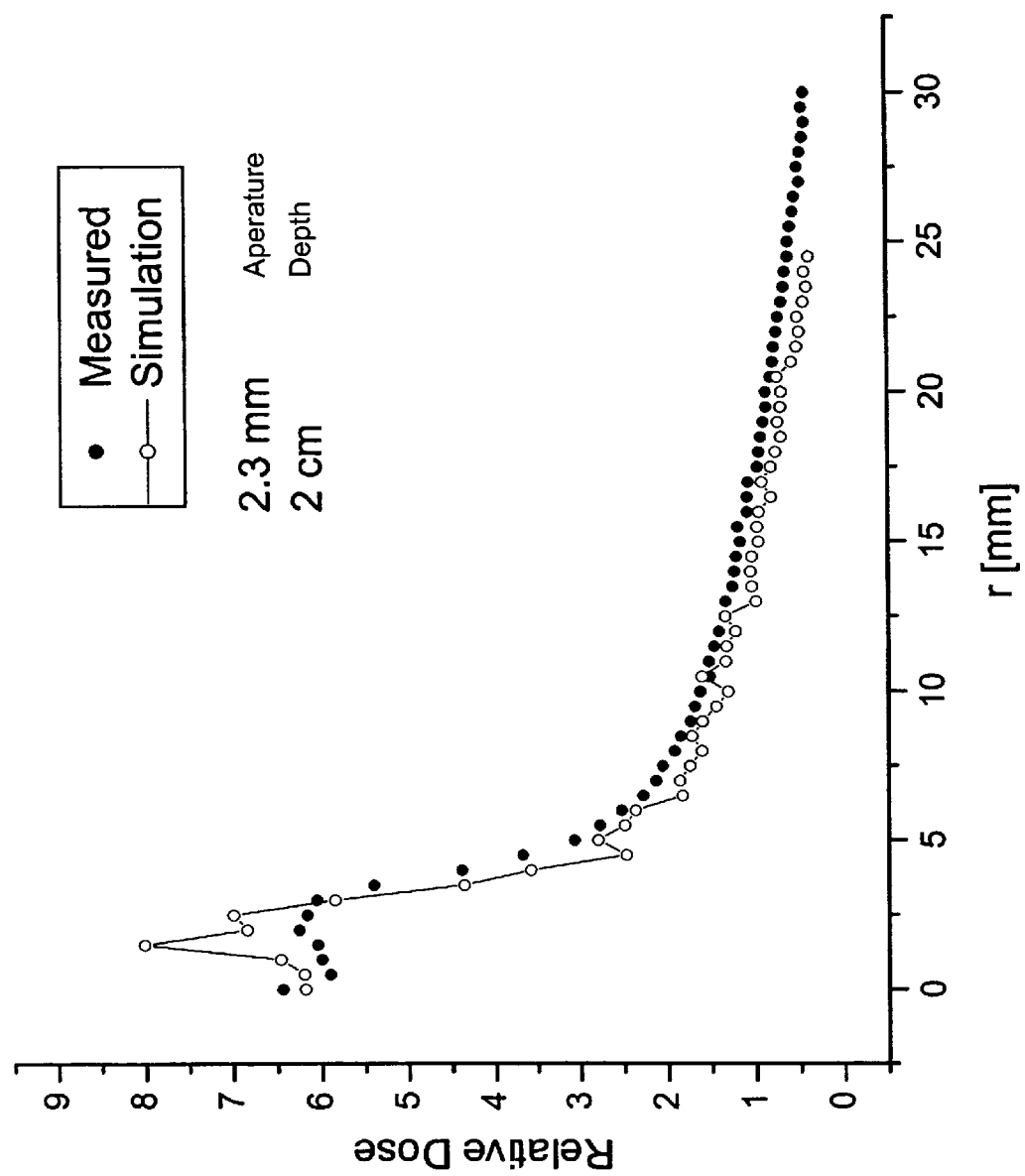
Figure 15:
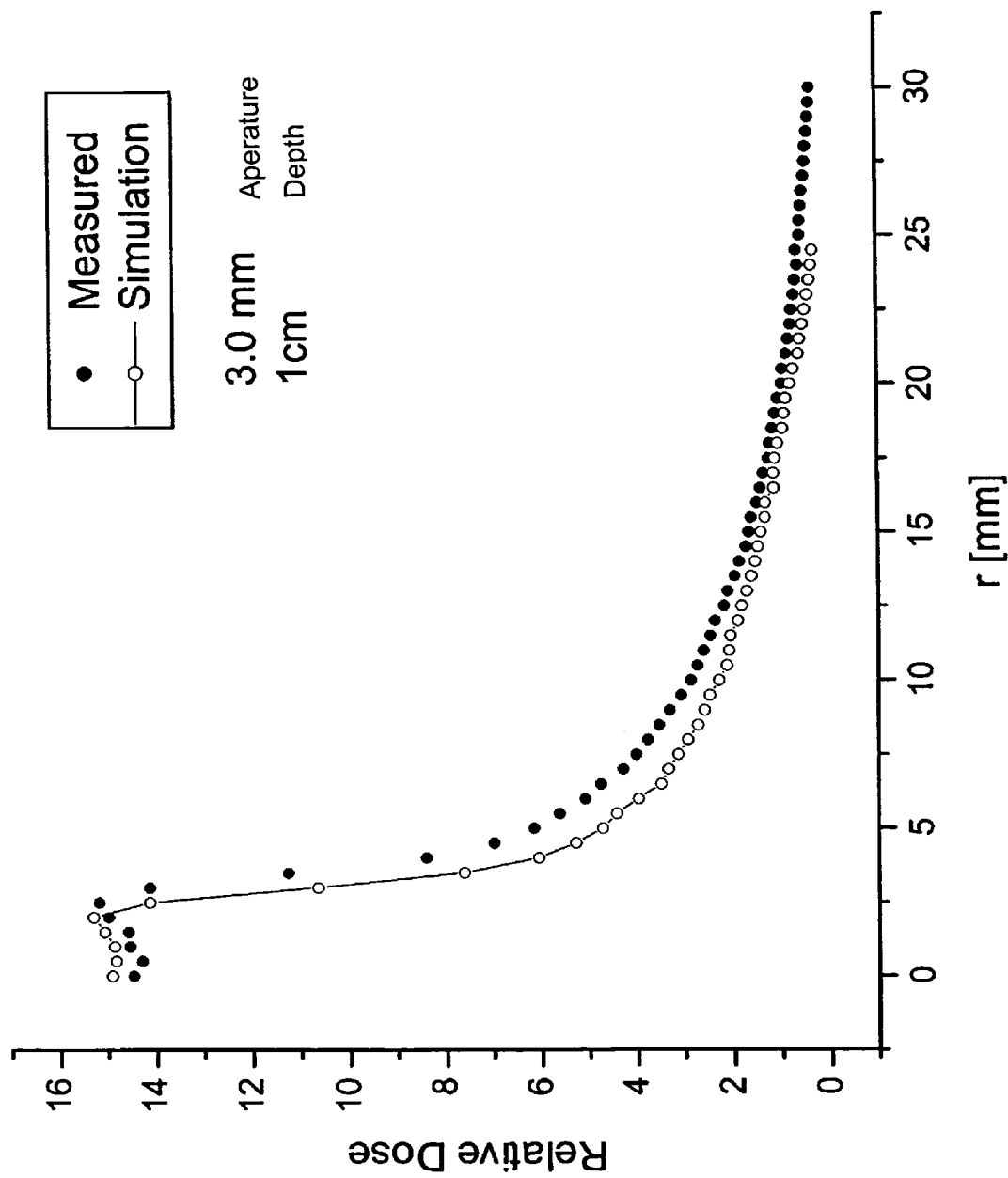
Figure 16:
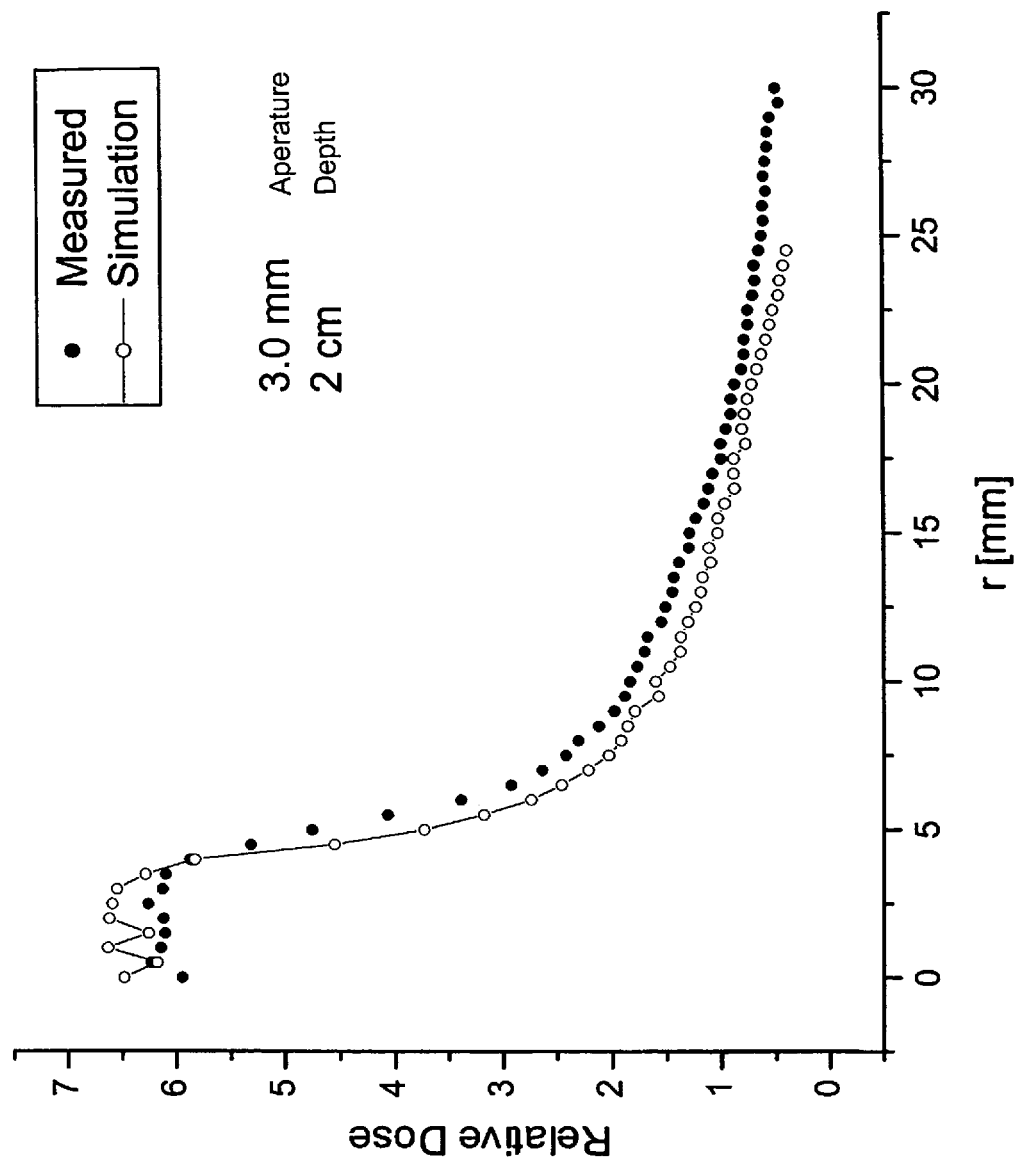
Figure 17:
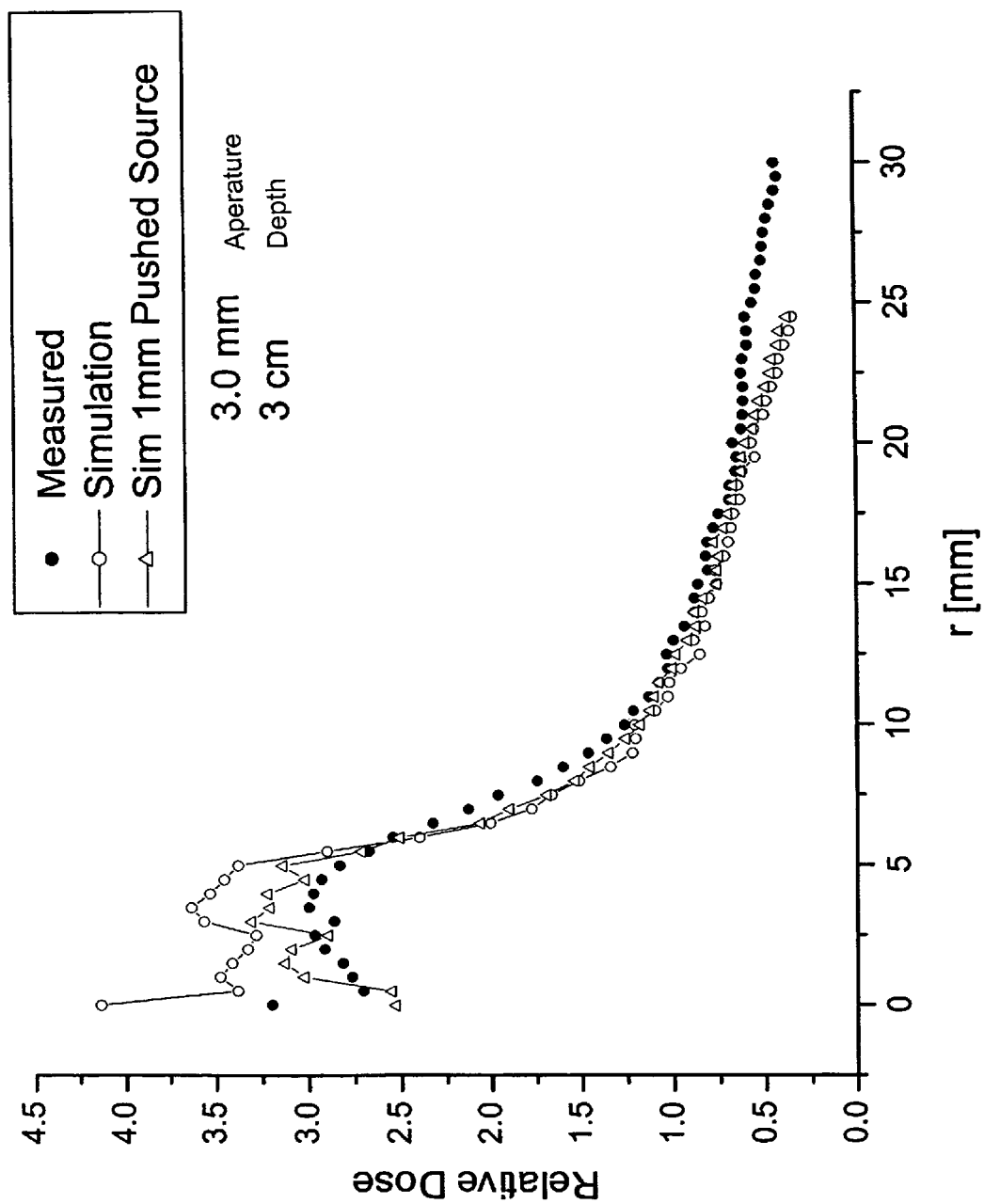

More in particular, FIG. 4 depicts equipment and geometry of a micro-irradiator therapy setup to validate MC simulation of high intensity $^{192}$Ir radionuclide brachytherapy source dose distributions. Collimator apertures of 1.0, 1.6, 2.3, and 3.0 mm diameter were tested in this test setup to validate a Monte Carlo ("MC") simulation. FIG. 5 depicts radiochromic film measured dose distribution data obtained from operation of the therapy setup depicted in FIG. 4.

FIGS. 6-17 are graphic comparisons of the measured and MC calculated radiated profile in water equivalent phantom for the test setup depicted in FIG. 4 wherein the MC results show good agreement with results obtained using the described test measurement geometry.

Figure 18:
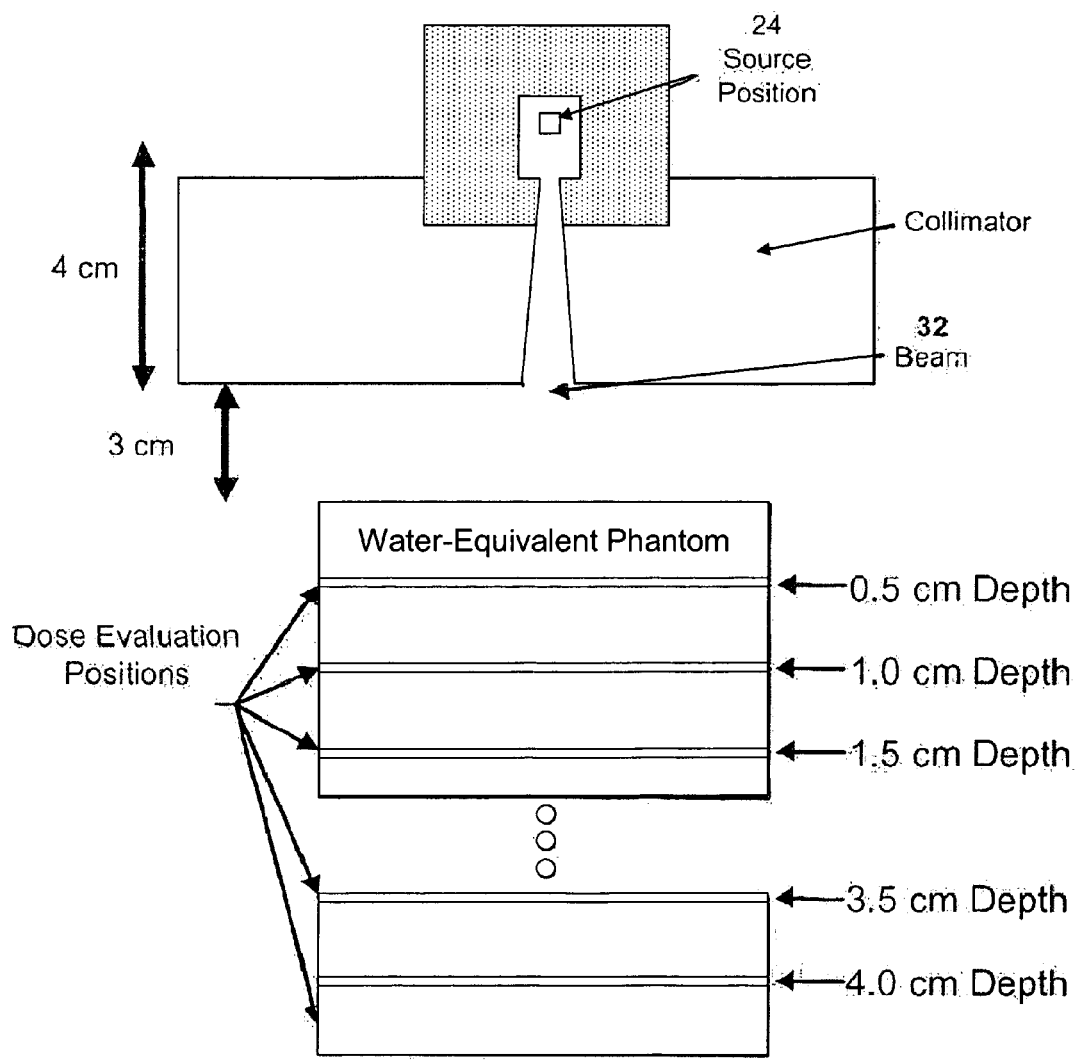
FIG. 18 is a schematic diagram of the geometry used in the simulations of the irradiation apparatus depicted in FIGS. 1-3 above.

FIG. 18 is a schematic diagram of the geometry used in the simulations of the irradiation apparatus depicted in FIGS. 1-3 above.

Figure 19:
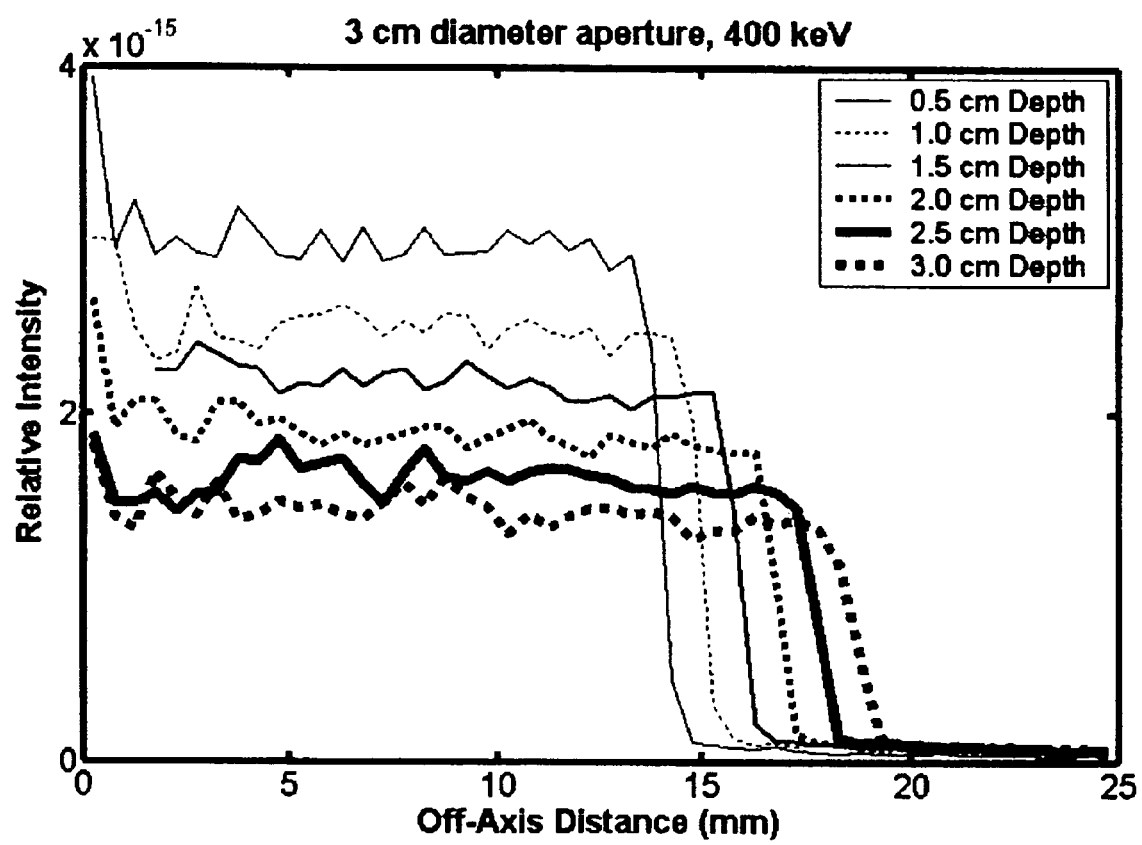
FIG. 19 depicts radial dose profiles as a function of collimator diameter obtained using a MC simulation for the geometry of the irradiation apparatus depicted in FIG. 18, using a functional 400 keV monoenergetic x-ray source.

FIG. 19 depicts radial dose profiles as a function of collimator diameter obtained using a MC simulation for the geometry of the irradiation apparatus depicted in FIG. 18, using a functional 400 keV monoenergetic x-ray source.

Figure 20:
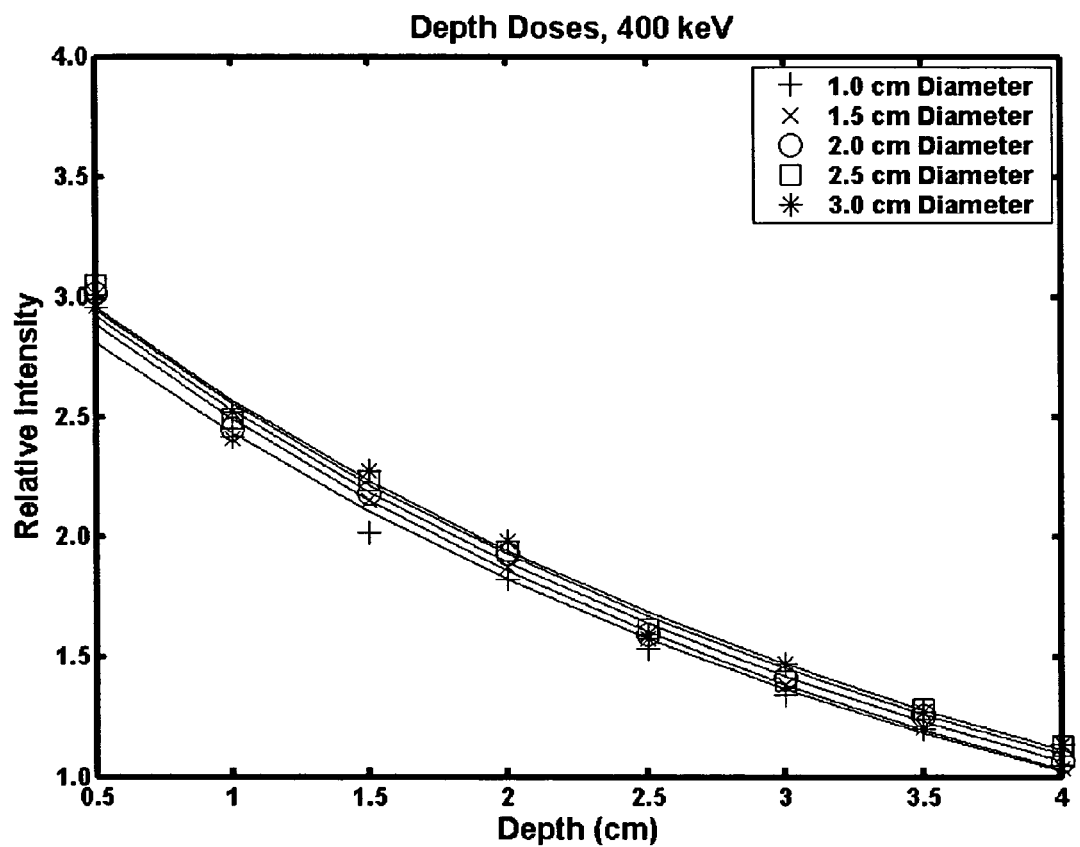
FIG. 20 depicts depth-dose characteristics of a simulated external brachytherapy irradiator using a 400 keV monoenergetic x-ray source as well as exponential fits to the depth dose data showing that the depth dose is relatively insensitive to aperture diameter.

FIG. 20 depicts depth-dose characteristics of a simulated external brachytherapy irradiator using a 400 keV monoenergetic x-ray source as well as exponential fits to the depth dose data showing that the depth dose is relatively insensitive to aperture diameter.

Figure 21:
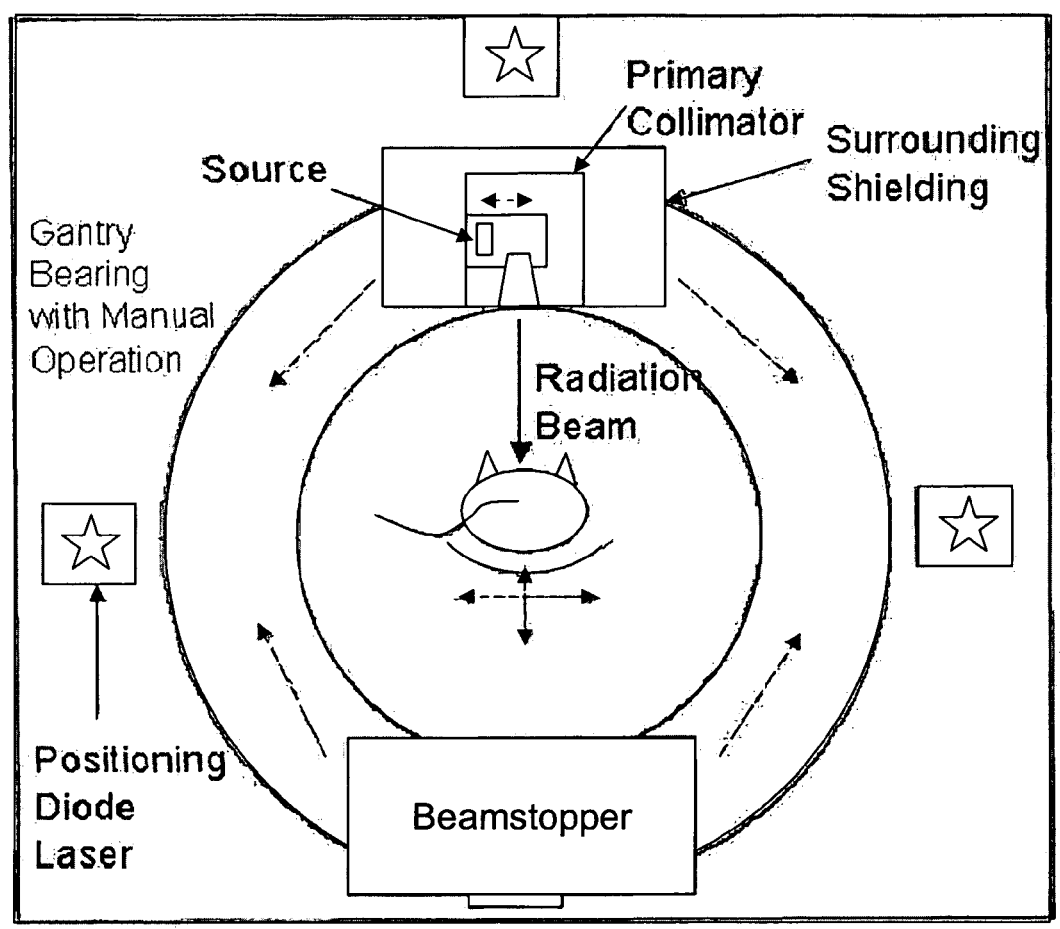
FIG. 21 depicts an irradiator using a high-activity $^{192}$Ir source that rotates around the animal.

FIG. 21 depicts an irradiator using a high-activity $^{192}$Ir source that rotates around the animal. The animal is placed on a moveable couch that adds flexibility to the treatment planning process. Monte Carlo dose simulations have been conducted to show the conformality available with the unit illustratively depicted in FIG. 1.

Figure 22:
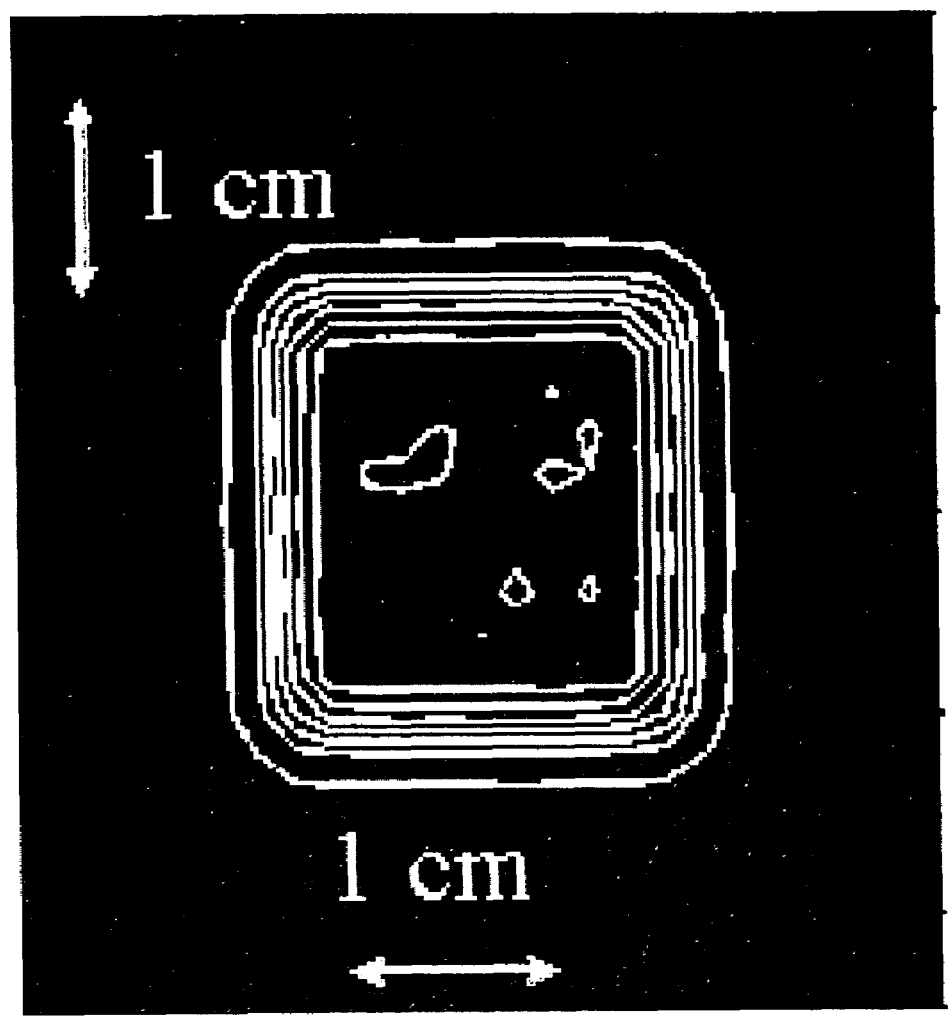
FIG. 22-23 depict the coronal and transverse cross-sections, respectively, through the dose distributions.
Figure 23:
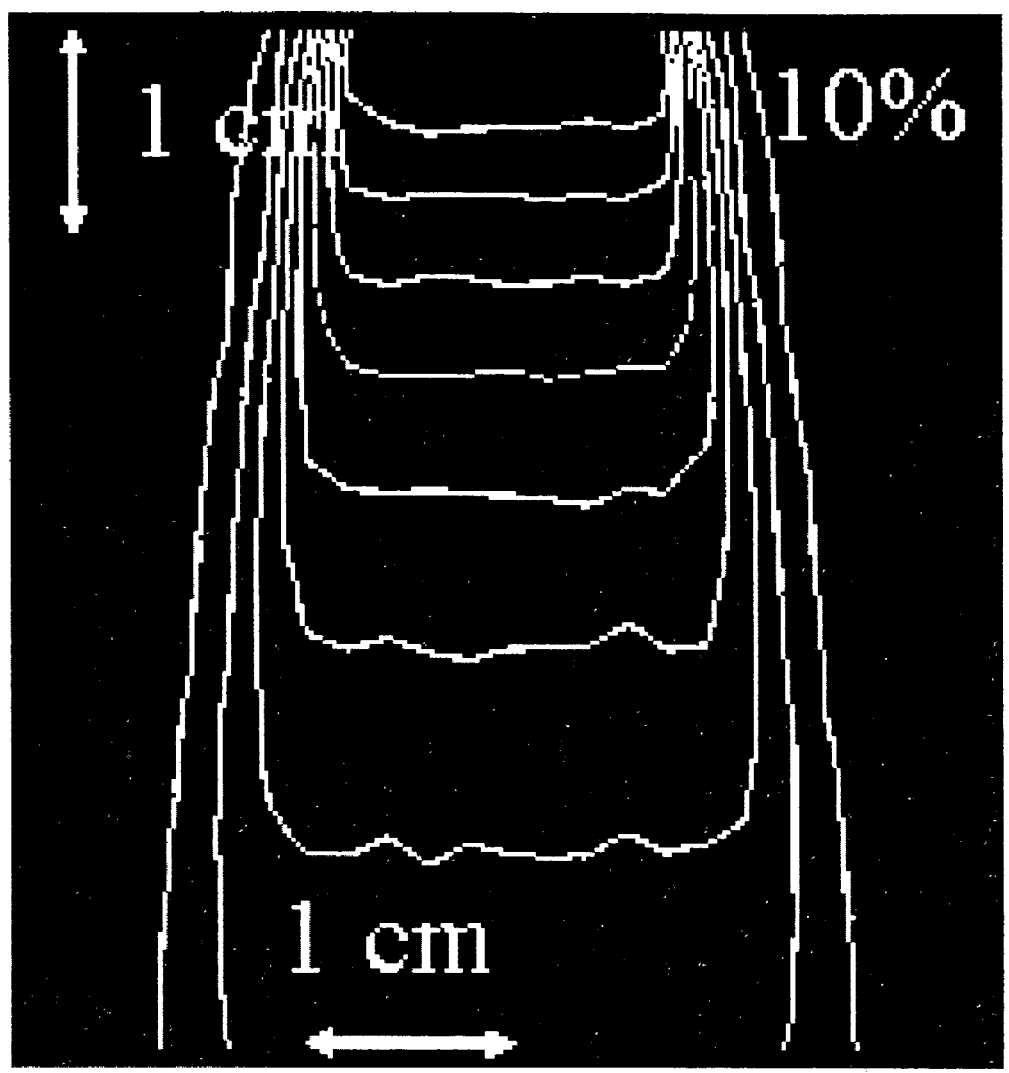
Figure 24:
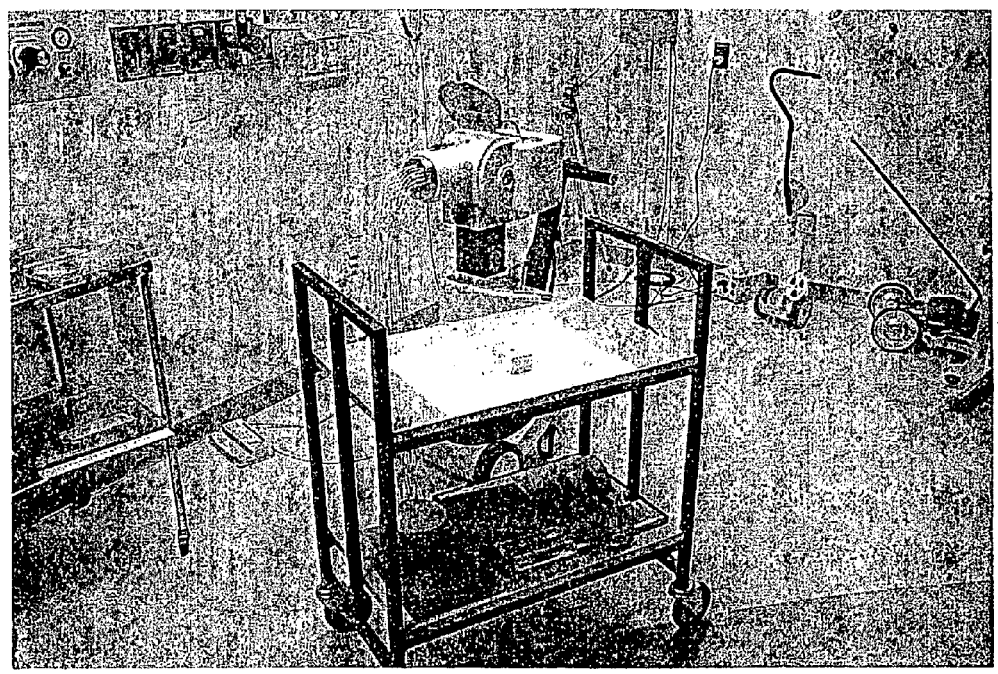
FIG. 24 depicts the setup for an animal irradiation using a prototype setup of the conformal irradiation of small animals.

FIG. 22-23 depicts the coronal and transverse cross-sections, respectively, through the dose distributions. Tests are shown below. These tests were conducted using a commercial $^{192}$Ir source from the Nucletron high-dose rate (HDR) remote afterloader (FIG. 24). The source is contained within a set of tubes and catheters. The end of the catheter is placed on a steel block on which is placed a Tungsten collimator. The collimator has a conical hole that collimates the radiation to a 1.5 cm diameter radiation field.

FIG. 24 depicts the setup for an animal irradiation using a prototype setup of the conformal irradiation of small animals.

A Nucletron HDR remote afterloader is shown with transfer tubes attached. One of the transfer tubes is attached to a catheter that is placed between the steel backing plate and the Tungsten collimator. Sitting on the collimator is a plastic sheet that supports the animal and serves as the couch. In this setup the Nucletron High Dose Rate brachytherapy machine is used to deliver effective radiation therapy using such aforedescribed catheters. The radioactive source is positioned beneath the collimator. The mouse is placed above the collimator opening to deliver intense controlled doses of radiation to the target portion of the mouse. A radioactive source emits radiation which passes through the catheter delivering intense controlled predetermined doses of radiation to the target portion of the mouse.

Figure 25:
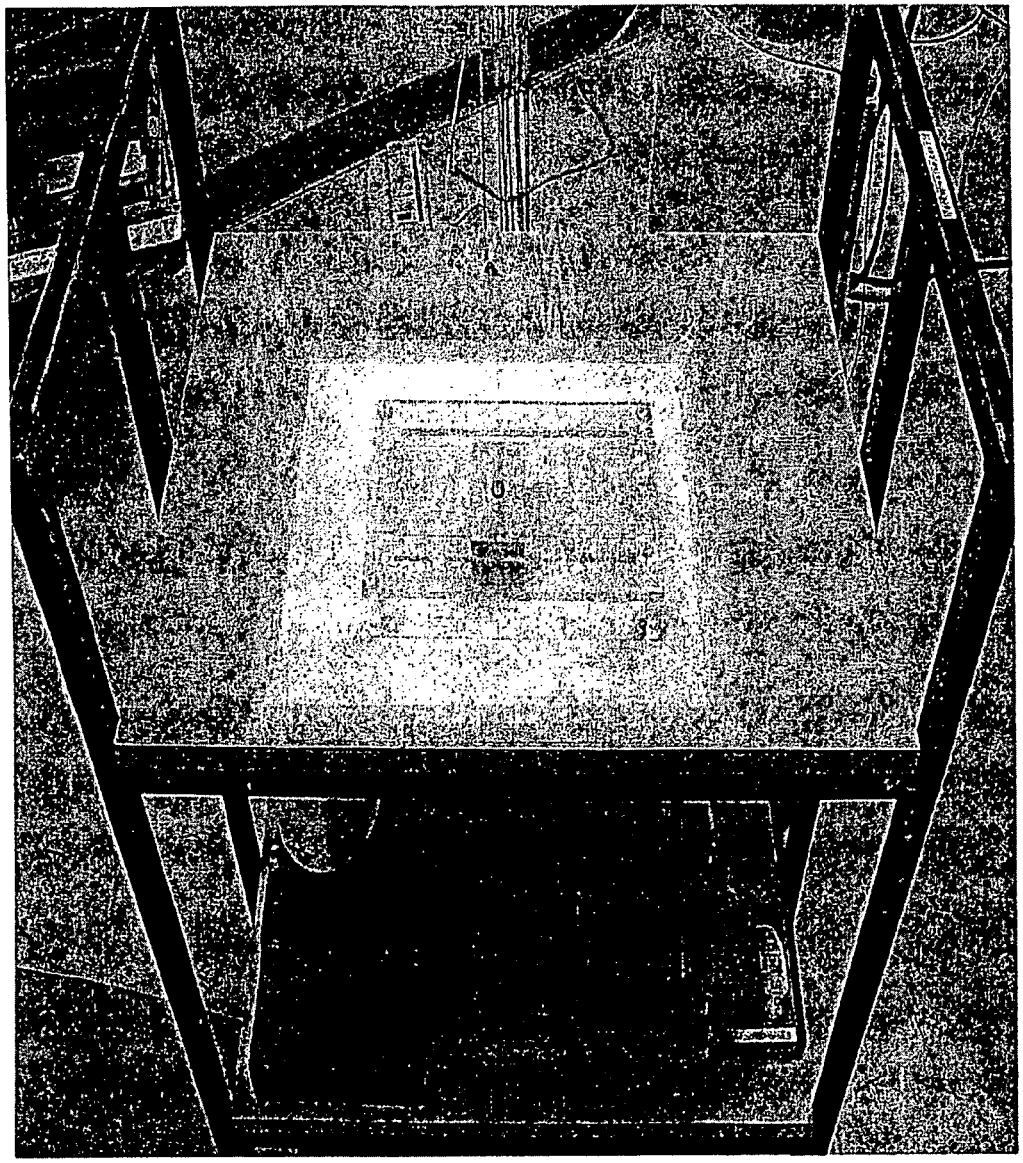
FIG. 25 depicts a close-up of the Tungsten collimator shown in FIG. 24.

FIG. 25 depicts a close-up of the Tungsten collimator shown in FIG. 24. The collimator includes a plurality of layers of Tungsten and a steel backing plate. The collimator is held together with tape. The collimator hole is visible as is the source-transfer catheter extending out the top of the image.

Figure 26:
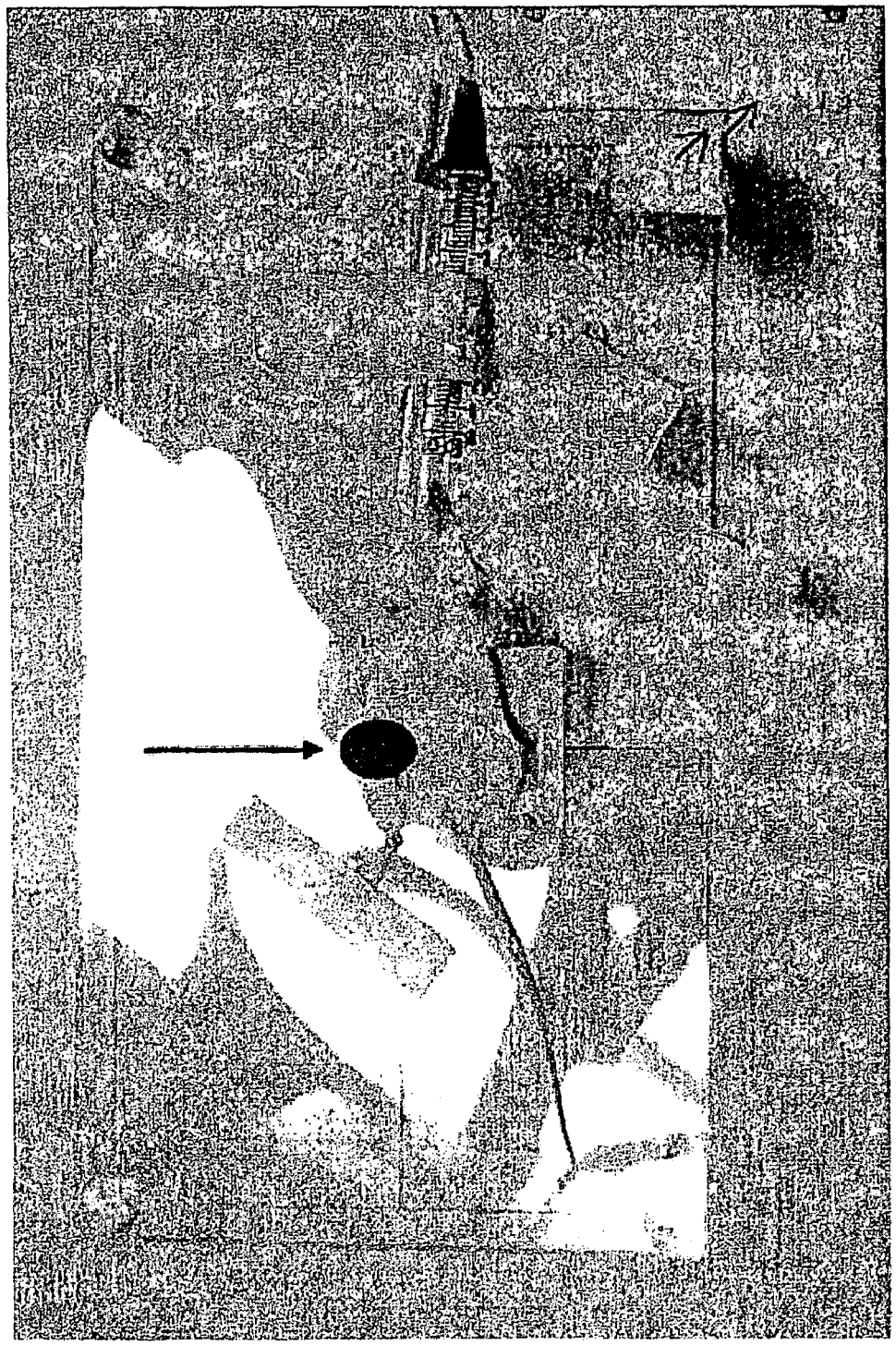
FIG. 26 is a close up of a mouse shown placed on the collimator system of FIGS. 24 and 25, and where the mouse is under general anesthesia.

FIG. 26 is a close up of a mouse shown placed on the collimator system of FIGS. 24 and 25, and where the mouse is under general anesthesia. An oval indicates the approximate radiation field projected outline. As can be seen, the collimator provides for an accurate localization of radiation to the mouse.

Figure 27:
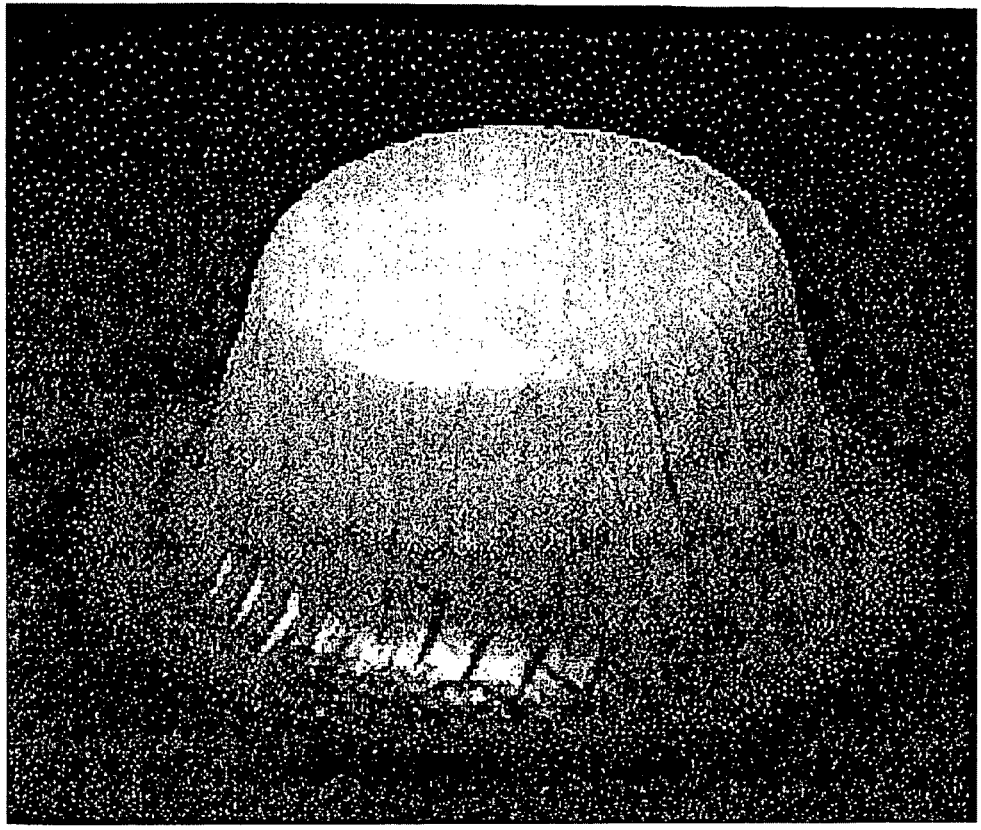
FIGS. 27 and 28 depict dosimetry measurements of the radiation profile distribution.
Figure 28:
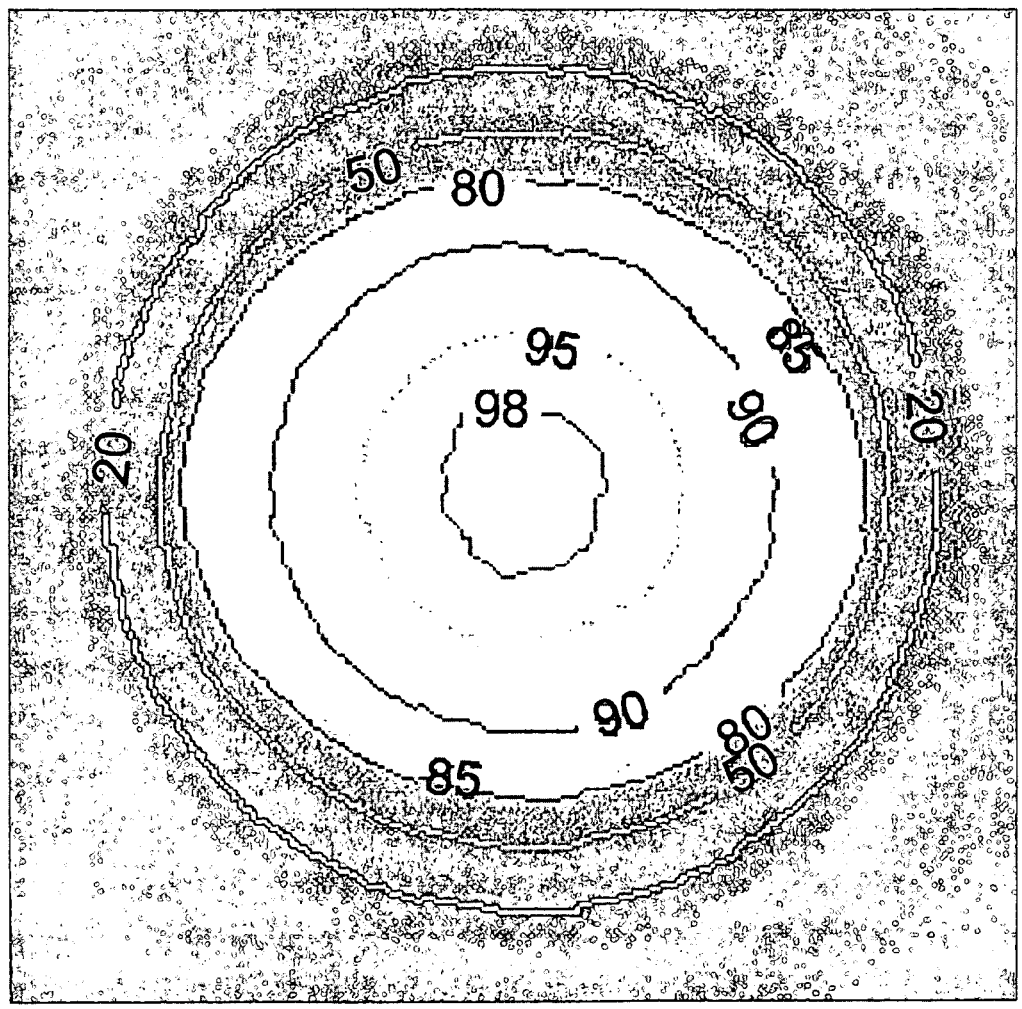

FIGS. 27 and 28 depict dosimetry measurements of the radiation profile distribution. The radiation field is remarkably flat (homogeneous) within the collimated field. The isodose distribution indicates the percentage of the maximum dose within the measured plane.

Figure 29:
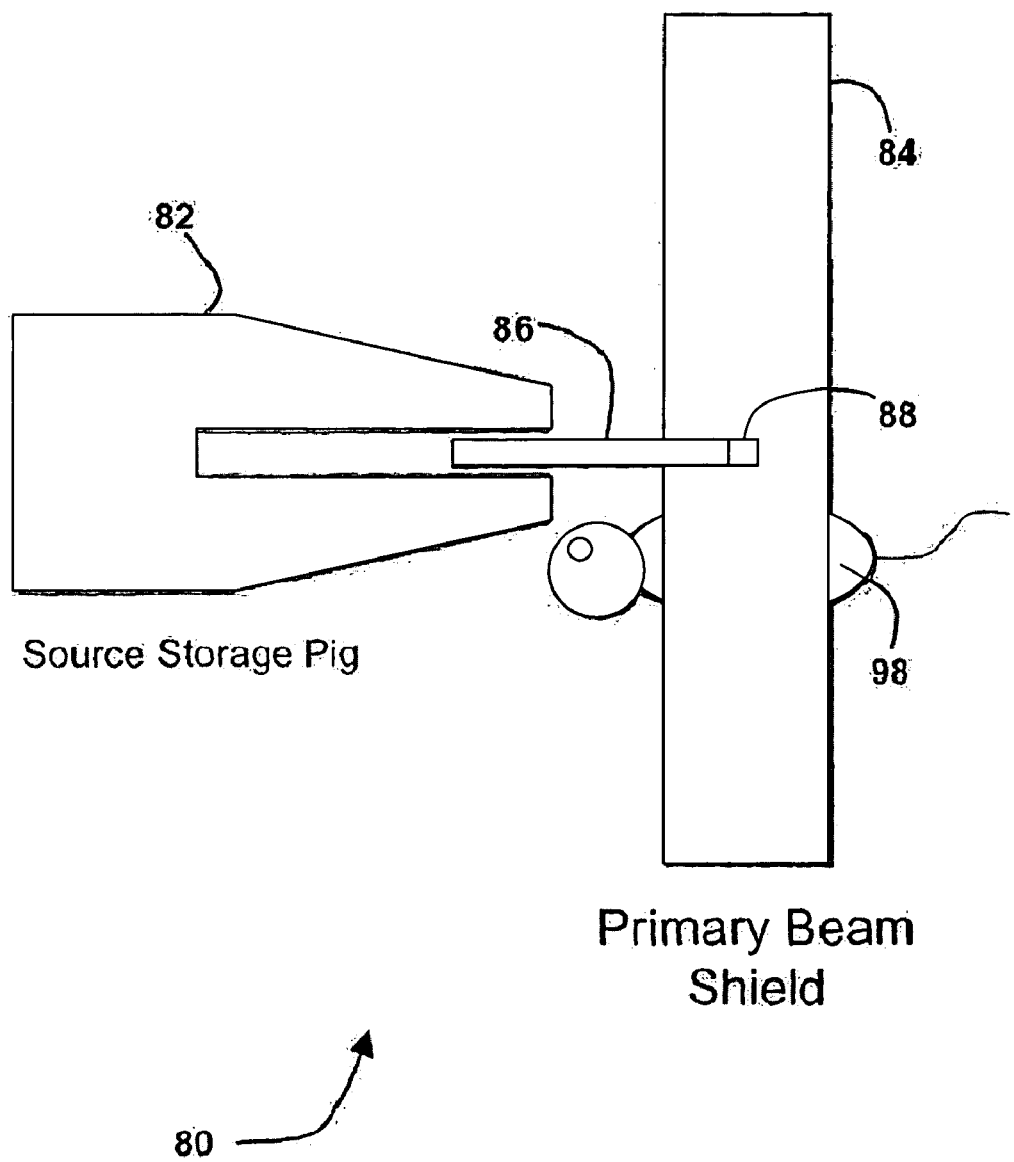
FIG. 29 is a side view of one embodiment of a non-human mammal conformal radiation therapy system.
Figure 30:
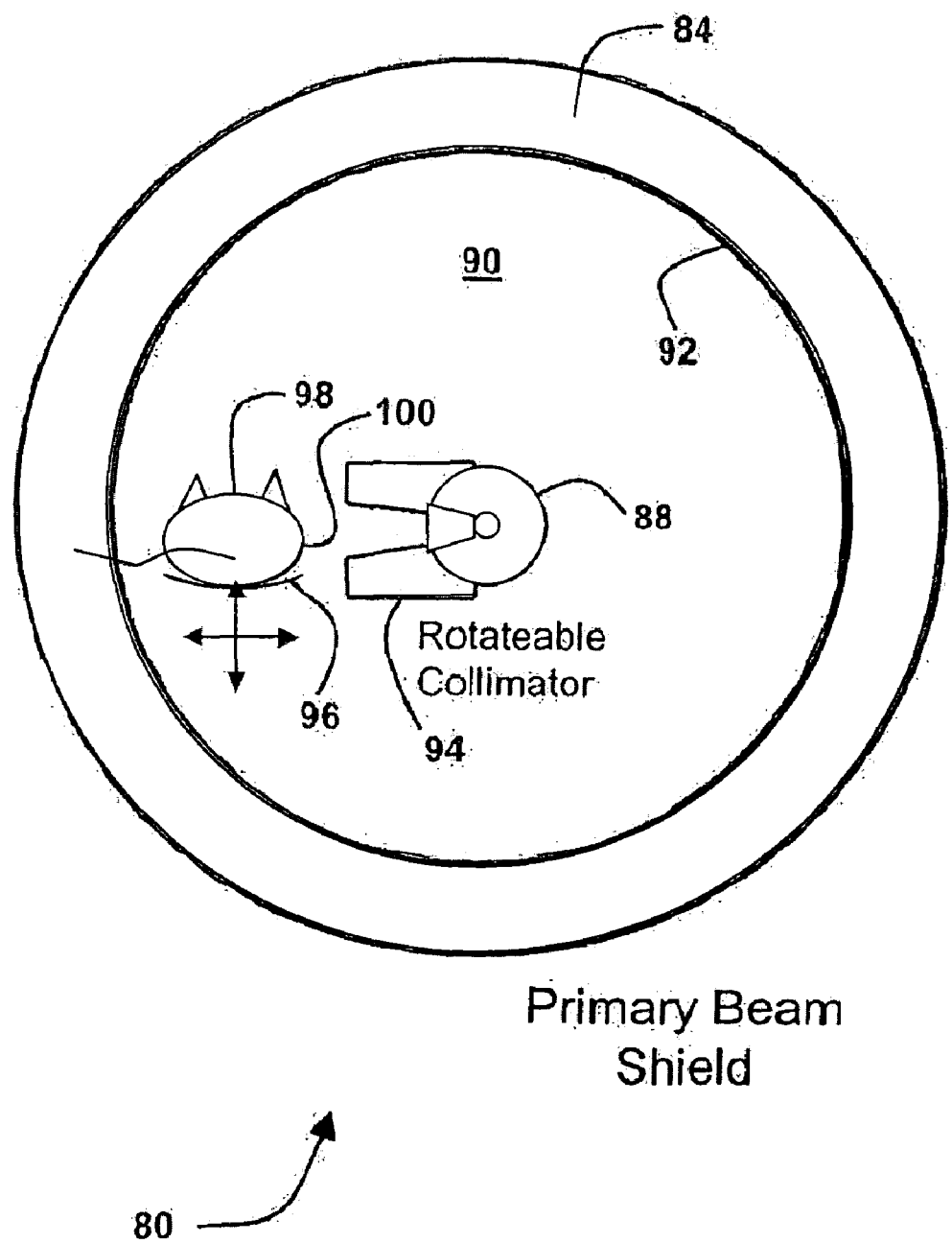
FIG. 30 is a front view of the embodiment of a non-human mammal conformal radiation therapy system shown in FIG. 29.

FIG. 29 is a side view and FIG. 30 is a front view of one embodiment of a non-human mammal conformal radiation therapy system 80. System 80 includes a source storage unit 82 and an enclosure 84. A retractable mechanical apparatus 86 is positioned and configured position a radioactive source 88 substantially within enclosure 84.

In an exemplary embodiment, apparatus 86 is configured to position source 88 using a linear motion such that source 88 is substantially centered in a bore 90 defined by an inner circumference 92 of enclosure 84. A collimator 94 is rotatably mounted to rotate around source 88 when source 88 is positioned substantially centered in bore 90. System 80, in one embodiment, further includes a couch 96 translatable in at least two dimensions. In one embodiment, bore 90 has a diameter less than about 30 cm and greater than about 1 cm.

In use, a non-human mammal 98 is positioned on couch 96 and couch 96, source 88, and collimator 94 are accurately positioned such that a desired portion 100 of mammal 98 is exposed to a calculated radiation dose. In an exemplary embodiment, the dose is a 3D dose calculation. In one embodiment, the dose is calculated from a 3D image of mammal 98. The 3D image can be from any imaging modality. In one embodiment, mammal 98 is positioned a distance between 1 cm and 15 cm from source 88. Note that while mammal 98 is shown in FIG. 30 positioned on the left side of source 88 to receive radiation on the right side of mammal 98, mammal 98 may be positioned on the right side of, above, and/or below source 88, and collimator 94 can be rotated such that any desired portion of mammal 98 can be irradiated with conformal radiation.

In an exemplary embodiment, apparatus 86 is configured to provide a visual indication of source 88 being outside of source storage unit 82. When source 88 is not being used, retractable mechanical apparatus 86 positions source 88 within source storage unit 82. In an exemplary embodiment, source 88 movement and collimator 94 rotation are computer controlled. For example, a user determines a radiation dose calculation and a desired portion of mammal 98 to apply the calculated dose, and provides this information to a computer (not shown) controlling rotatable collimator 94 and apparatus 86. The computer then moves table 96, source 88, and collimator 94 such that the portion receives conformal radiation at the calculated dose.

Figure 31:
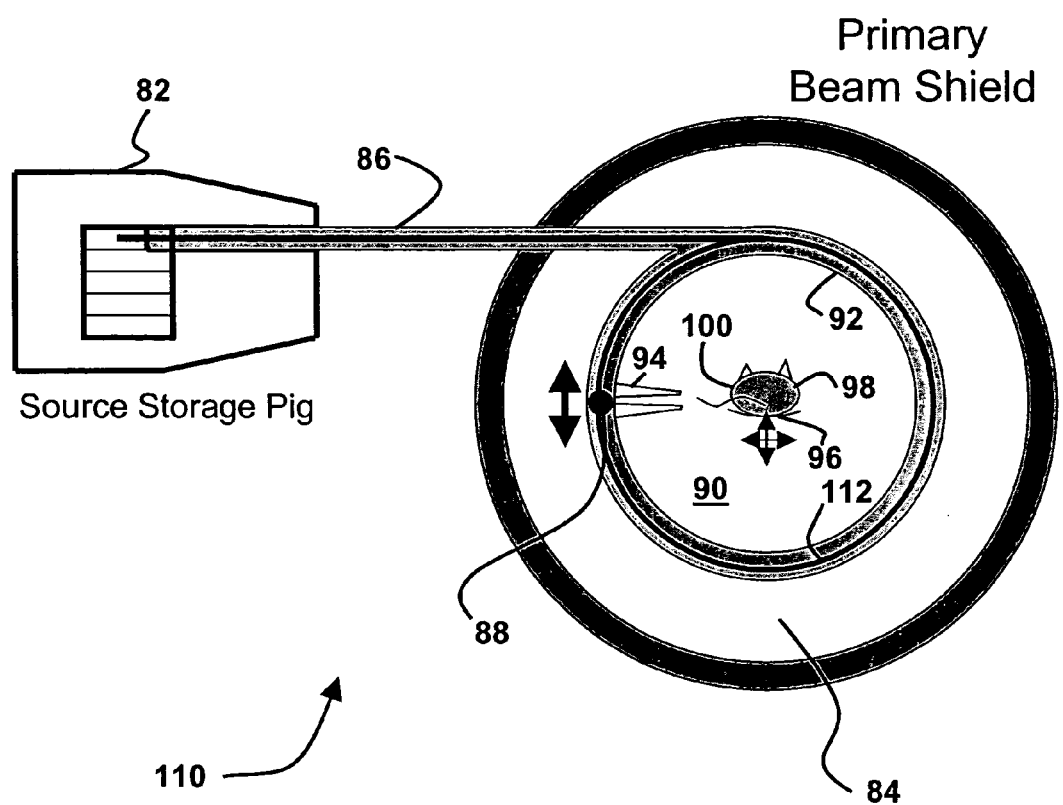
FIG. 31 is a side view of one embodiment of a non-human mammal conformal radiation therapy system.

FIG. 31 is a front view of one embodiment of a non-human mammal conformal radiation therapy system 110 similar to system 80 where like elements are similarly numbered. System 110 includes a source storage unit 82, a retractable mechanical apparatus 86, and a radioactive source 88. A table 96 translatable in two dimensions is positioned within a bore 90 of an enclosure 84. System 110 includes a circular source path 112 proximate an inner circumference 92 of bore 90 and a collimator 94 positioned to collimate radiation emitted from source 88. In an exemplary embodiment, collimator 94 is configured to move adjacent circular path 112 such that source 88 and collimator 94 are positionable anywhere along path 112 to deliver conformal radiation to all portions of a non-human mammal 98.

In another exemplary embodiment, system 110 includes a plurality of collimators 94 fixed positioned at a plurality of positions along path 112 such that only source 88 moves for application of conformal radiation to any desired portion of mammal 98. In one embodiment with the plurality of fixed collimators 94, each collimator 94 includes a movable radiation shield such that radiation is not emitted from collimators 94 being passed by source 88 while source 88 is being moved to a particular desired collimator 94. After source is positioned at the desired collimator 94, the shield is opened and the desired portion of mammal 98 receives conformal radiation. In one embodiment, bore 90 has a diameter less than about 30 cm.

In use, a non-human mammal 98 is positioned on couch 96 and couch 96, source 88, and collimator 94 are accurately positioned such that a desired portion 100 of mammal 98 is exposed to a calculated radiation dose. In an exemplary embodiment, the dose is a 3D dose calculation. In one embodiment, the dose is calculated from a 3D image of mammal 98. The 3D image can be from any imaging modality. In one embodiment, mammal 98 is positioned a distance between 1 cm and 15 cm from source 88.

Note that while mammal 98 is shown in FIG. 31 positioned on the right side of source 88 to receive radiation on the left side of mammal 98, source 88 may be positioned on the left side of, above, andlor below mammal 98, and collimator 94 can be positioned such that any desired portion of mammal 98 can be irradiated with conformal radiation. In an exemplary embodiment, apparatus 86 is configured to provide a visual indication of source 88 being outside of source storage unit 82. When source 88 is not being used, retractable mechanical apparatus 86 positions source 88 within source storage unit 82. In an exemplary embodiment, source 88 movement and collimator 94 position are computer controlled. For example, a user determines a radiation dose calculation and a desired portion of mammal 98 to apply the calculated dose, and provides this information to a computer (not shown) controlling collimator 94 and apparatus 86. The computer then moves table 96, source 88, and collimator 94 such that the portion receives conformal radiation at the calculated dose. In the embodiment with a plurality of collimators, the computer determines which collimator 94 to use and positions source 88 and mammal 98 such that the desired portion of mammal 98 receives conformal radiation. Alternatively, the user determines which collimator 94 to use and instructs the computer which collimator to use and the calculated dose, the computer than moves source 88 to the user selected collimator and positions couch 96 such that the desired portion receives conformal radiation at the calculated dose.

EXAMPLES

The present invention is more particularly described in the following examples which are intended as illustrative only since numerous modifications and variations therein will be apparent to those skilled in the art.

An optimum set of geometric parameters for the primary collimator and radiation source of the apparatus depicted in FIG. 1 has been provided by the use of MC simulation by validating a MC simulation against real data obtain from a setup and utilizing the MC simulation to provide the parameters.

An MC simulation was done on the setup depicted in FIG. 4. When the results of this MC simulation were compared with actual data from a test setup depicted in FIG. 4, it was concluded that the MC simulation was validated. Thereafter an MC simulation was done on the apparatus depicted in FIG. 1 to provide operating designs and parameters.

These FIGS. 6-17 above describe the test results from use of an MC simulation done on the test setup depicted in FIG. 4. The figures provide test data obtained from the setup.

Monte Carlo (MC) simulation is a mature and well-established technique for obtaining dose distributions in various geometry's. We used the BEAMnrc Monte Carlo code for modeling the dose from a $^{192}$Ir source. The $^{192}$Ir source was obtained from Nucletron.

FIGS. 24-28 show an example of a micro-radiation therapy irradiator used to irradiate a set of five mice with tumors implanted in the flank. The mice were irradiated to a dose of 20 Gy using the dose distribution shown in FIGS. 27 and 28. An insubstantial dose was delivered to the body of the mice. Five mice were also implanted with tumors and not irradiated as controls. The mice were subsequently imaged using a microPET imager each day for four days after irradiation. After irradiation the irradiated mice showed no symptoms of radiation sickness due to the conformal nature of the radiation dose delivery. The images (not shown) indicated a tumor regression of half for the irradiated mice with no regression of the unirradiated mice. This experiment indicates the quantitative aspect and utility of micro-radiation therapy.

A target such as a small animal receiving radiation therapy, is bombarded by trillions of particles. In an aspect, Monte Carlo radiation transport algorithms can determine the dose deposited in the target by following the path of representative particles as they travel through the irradiator, biological sample, and other materials in the radiation's path. MC predicts a distribution of how these particles and their progeny products interact in matter. Researchers sample millions of particles that enter the biological sample and record the energy deposited by each as it travels through the sample, and so Monte Carlo (MC) statistical method develops an accurate representation of the dose distribution.

Data used in the MC simulation comprises a library of data on nuclear science and radiation taken by researchers in the past on other equipment and apparatus.

At the current level of computer technology, it is feasible to employ clusters of relatively inexpensive workstations for the complex MC calculations a cluster of 24 PC's (AMD Athlon XP 1.53 GHz, 512 MB per node) running BEAMnrc MC code, have been used to simulate a radiation source and collimator, which is used for the conformal therapy of small animals. A simulation calculates multiple scenarios of a model by repeatedly sampling values from the probability distributions for the uncertain variables and using those values for the cell. A simulation calculates multiple scenarios of a model by repeatedly sampling values from the probability distributions for the uncertain variables and using those values for the cell.

BEAMnrc is a general purpose Monte Carlo simulation system for modelling radiotherapy sources which is based on the EGSnrc code system for modelling electron and photon transport.

For simulation, the collimator is assumed to irradiate a water phantom with a 1 cm air gap. A radial dose profile was scored in a 2 cm deep plane in the phantom water.

In an aspect, a water phantom is a radiation data acquisition system. Such water phantom systems make measuring of pulsed photon and electron radiation from all types of accelerators and continuous radiation from Co-60 and Cs-137 teletherapy units easy and accurate. The user is provided with a material that is common, inexpensive, and readily available anywhere in the world. It also has radiological properties similar to animal and human tissues. There are commercial plastics (such as Solid Water) that mimic the radiation properties of water for purposes of experimentation where a liquid medium is impractical.

The measurement system was radiochromic film, positioned between sheets of water-equivalent plastic.

In this Example, the ratio of collimator to source diameters was varied and the resulting radial dose profiles were compared. The simulation time was approximately 2 hours per given geometry ($2 \times 10^9$ histories) on a 24 node computer cluster. Preliminary results show a high sensitivity of the radial dose profile to the ratio of source and collimator exit aperture diameters. It was observed that the radial dose profile increases in sharpness with the decreasing source radius, highlighting the necessary tradeoff between the beam quality and achievable dose rate. The model is based on a cylindrically shaped $^{192}$Ir source, but other suitable radioisotopes will be investigated. This technique promotes the use of this Monte Carlo code as a rapid prototyping tool.

The simulation shows that the MC code accurately models the actual physical setup (FIG. 4). The MC code was then used to simulate a more realistic irradiator geometry (FIG. 18). The simulations were conducted using a 400 keV mono-energetic point source (similar energy to $^{192}$Ir) and irradiating a water phantom using different diameter apertures. FIG. 19 shows the profiles from a 3.0 cm diameter aperture for different depths in water. Unlike the previous simulation, the distance between the source and water was increased to a more appropriate distance. The profiles are very sharp, indicating that if the source is small enough, the radiation dose distribution is highly conformal.

The simulation also showed the depth-dose characteristics of the irradiator. FIG. 20 shows the depth-dose of the 400 keV simulation for portal diameters ranging from 1.0 to 3.0 cm. These show that there is little dependence of the depth dose on field size. Also, the depth dose nicely matches the size of small animals relative to clinical x-ray beams for human treatments.

The Tungsten collimator limited the volume of the mouse receiving high radiation doses to the conical region subtending the collimator opening. The personnel conducting the experiment were shielded by placing the experimental apparatus in a shielded radiation vault that had been designed to shield the $^{192}$Ir source used in the experiment.

The required strength of the radioactive source is determined using Monte Carlo dose distribution simulations. After an initial design has been determined, low-activity sources are fabricated and the dose rate per unit source strength is determined experimentally. The required source strength is then determined by the multiplying the experimental source strength by the ratio of desired dose rate to experimental dose rate.

It will be apparent to those skilled in the art that various modifications and variations can be made in the present invention without departing from the scope or spirit of this discovery. Other embodiments of the invention will be apparent to those skilled in the art from consideration of the specification and practice of the invention disclosed herein. It is intended that the specification and examples be considered as exemplary only.

A micro-radiation therapy apparatus comprises an isotope-based micro-radiotherapy irradiator useful for radiating a target biological system, the irradiator having a radiation source proximate the target biological system and comprising an adjustable collimated radiation beam.

A collimator configured to collimate a radiation beam in an isotope-based micro-radiotherapy brachytherapy irradiator apparatus comprising an adjustable robotic arm supporting a metal shield apparatus housing a radioactive source projecting a radiation beam and having a selectable exit portal for radiation emanating from the radioactive source (FIG. 1).

A method of treating neoplastic tissue by effectively irradiating at least one neoplastic cell in a biological system comprises applying micro-radiation from an isotope-based micro-radiation irradiator, the irradiator having an external radiation source proximate the biological system comprising a collimated radiation beam to a target cell of the biological system whereby the neoplastic cell is made non-neoplastic.

Advantageously the herein described methods and apparatus allow one to take advantage of the available impressive imaging resolution technology. For members of the small animal classification, such as cell cultures, accurate irradiation using a dose distribution with a controlled variation in intensity and spatial extent is now possible. The irradiators of this discovery are useful to treat small animals and support the numerous radiation response tests when and if needed.

What is claimed is:

1. A non-human mammal conformal radiation therapy system comprising an enclosure comprising a bore having a diameter less than about 30 centimeters, a radioactive radiation source, a retractable mechanical apparatus positioned and configured to position said source substantially within said enclosure and at a distance between 1 centimeter and 15 centimeters from a non-human mammal and to retract said source to a source storage unit, and a collimator positioned to collimate radiation emitted from said source.

2. A system in accordance with claim 1 wherein said retractable mechanical apparatus is further configured to position said source substantially centered in said bore using a linear motion, said collimator rotatably mounted to rotate around said source when said source is positioned and centered in said bore.

3. A system in accordance with claim 1 wherein said retractable mechanical apparatus is further configured to position said source proximate an inner circumference of said bore using at least partially a circular motion.

4. A system in accordance with claim 1 further comprising a couch translatable in at least two dimensions within said bore and configured to position the non-human mammal.

5. A non-human mammal conformal radiation therapy system comprising: an enclosure comprising a bore having a diameter less than about 30 centimeters; a radioactive radiation source; a retractable mechanical apparatus positioned and configured to position said source substantially within said enclosure and at a distance between 1 centimeter and 15 centimeters from a non-human mammal; and a collimator unit positioned to collimate radiation emitted from said source, wherein said retractable mechanical apparatus is further configured to move said source within said collimator unit such that substantially no un-collimated radiation is emitted.

6. A system in accordance with claim 5 wherein said retractable mechanical apparatus is further configured to position said source proximate an inner circumference of said bore using at least partially a circular motion.

7. A system in accordance with claim 6 further comprising a plurality of collimators positioned proximate the inner circumference, wherein said retractable mechanical apparatus is further configured to position said source proximate to any desired collimator.

8. A system in accordance with claim 5 further comprising a plurality of collimators positioned proximate an inner circumference of said bore, wherein said retractable mechanical apparatus is fiuther configured to position said source proximate to any desired collimator.

9. A system in accordance with claim 8 further comprising a couch translatable in at least two dimensions within said bore and configured to position the non-human mammal.

10. A system in accordance with claim 5 further comprising a couch translatable in at least two dimensions within said bore and configured to position the non-human mammal.

* * * * *